(12) United States Patent
Cardin

(10) Patent No.: US 11,896,366 B2
(45) Date of Patent: Feb. 13, 2024

(54) VENTILATOR-COUPLED SAMPLING DEVICE AND METHOD

(71) Applicant: Entech Instruments Inc., Simi Valley, CA (US)

(72) Inventor: Daniel B. Cardin, Simi Valley, CA (US)

(73) Assignee: Entech Instruments Inc., Simi Valley, CA (US)

( * ) Notice: Subject to any disclaimer, the term of this patent is extended or adjusted under 35 U.S.C. 154(b) by 1291 days.

(21) Appl. No.: 16/294,325

(22) Filed: Mar. 6, 2019

(65) Prior Publication Data

US 2019/0274588 A1 Sep. 12, 2019

Related U.S. Application Data

(60) Provisional application No. 62/639,479, filed on Mar. 6, 2018.

(51) Int. Cl.
*A61B 5/097* (2006.01)
*A61M 16/20* (2006.01)
(Continued)

(52) U.S. Cl.
CPC .............. *A61B 5/097* (2013.01); *A61B 5/082* (2013.01); *A61M 16/0057* (2013.01);
(Continued)

(58) Field of Classification Search
None
See application file for complete search history.

(56) References Cited

U.S. PATENT DOCUMENTS 2,985,007 A 5/1961 Jan
4,170,901 A 10/1979 Conkle et al.
(Continued)

FOREIGN PATENT DOCUMENTS

CN 2789754 Y 6/2006
CN 101793880 A 8/2010
(Continued)

OTHER PUBLICATIONS

Thomas, Kent W., Edo D. Pellizzari, and Stephen D. Cooper. "A canister-based method for collection and GC/MS analysis of volatile organic compounds in human breath." Journal of analytical toxicology 15.2 (1991): 54-59. (Year: 1991).*

(Continued)

*Primary Examiner* — Jacqueline Cheng
*Assistant Examiner* — Jairo H Portillo
(74) *Attorney, Agent, or Firm* — Kubota & Basol LLP

(57) ABSTRACT

A sample collection device collects Volatile Organic Compounds (VOCs) in exhaled breath in the outlet of a breathing assisted ventilator. The sample collection device is attached to the ventilator outlet line through a coupler containing either two check valves, or a check valve and a restrictive outlet flow path. During sampling, the exhaled air flows through a sorbent contained in the sample collection device as the ventilator pressure increases and decreases during the assisted breathing process. The flow of the exhaled air through the sample collection system is driven by the alternating pressure in the ventilator line without the need for an additional pump or power supply separate from the ventilator pump and power supply. The sample collection device can be used to monitor levels of bacteria-produced VOCs as an early detection of pneumonia and to allow feedback on the effectiveness of antibiotic treatment.

20 Claims, 14 Drawing Sheets

(51) Int. Cl.
  *A61M 16/08* (2006.01)
  *A61M 16/00* (2006.01)
  *A61B 5/08* (2006.01)
  *G01N 1/22* (2006.01)
  *G01N 33/497* (2006.01)
  *A61B 10/00* (2006.01)

(52) U.S. Cl.
  CPC ........ *A61M 16/085* (2014.02); *A61M 16/208* (2013.01); *A61B 2010/0087* (2013.01); *G01N 1/2214* (2013.01); *G01N 2001/2244* (2013.01); *G01N 2001/2285* (2013.01); *G01N 2033/4975* (2013.01)

(56) References Cited

U.S. PATENT DOCUMENTS

| | | |
|---|---|---|
| 4,213,326 A | 7/1980 | Brodasky |
| 4,249,904 A | 2/1981 | Reisch et al. |
| 4,300,393 A | 11/1981 | Stearns |
| 4,583,394 A | 4/1986 | Murakami et al. |
| 4,805,441 A | 2/1989 | Sides et al. |
| 4,849,179 A | 7/1989 | Reinhardt et al. |
| 5,081,871 A * | 1/1992 | Glaser .................... A61B 5/083 73/863.23 |
| 5,089,124 A | 2/1992 | Mahar et al. |
| 5,198,197 A | 3/1993 | Clay et al. |
| 5,288,310 A | 2/1994 | Peters et al. |
| 5,347,844 A | 9/1994 | Grob et al. |
| 5,363,707 A | 11/1994 | Augenblick et al. |
| 5,465,607 A | 11/1995 | Corrigan et al. |
| 5,496,741 A | 3/1996 | Pawliszyn |
| 5,711,786 A | 1/1998 | Hinshaw |
| 5,792,423 A | 8/1998 | Markelov |
| 5,847,291 A | 12/1998 | Green et al. |
| 5,866,004 A | 2/1999 | Houck et al. |
| 5,900,532 A | 5/1999 | Ikeda et al. |
| 5,952,557 A | 9/1999 | Ikeda et al. |
| 6,177,008 B1 | 1/2001 | Treiber et al. |
| 6,186,012 B1 | 2/2001 | Kenny |
| 6,351,983 B1 | 3/2002 | Haas et al. |
| 6,395,560 B1 | 5/2002 | Markelov |
| 6,484,560 B1 | 11/2002 | Prest |
| 6,649,403 B1 | 11/2003 | McDevitt et al. |
| 6,662,626 B2 | 12/2003 | Van Der Maas |
| 6,677,129 B1 | 1/2004 | Blume |
| 6,708,550 B2 | 3/2004 | Mcgee et al. |
| 6,726,637 B2 | 4/2004 | Phillips |
| 6,770,246 B1 | 8/2004 | Husek |
| 6,814,785 B2 | 11/2004 | Tipler et al. |
| 7,329,393 B2 | 2/2008 | Backes et al. |
| 7,464,614 B2 | 12/2008 | Harvey |
| 7,568,401 B1 | 8/2009 | Berends, Jr. |
| 7,674,631 B2 | 3/2010 | Pawliszyn |
| 7,700,045 B2 | 4/2010 | Skarping et al. |
| 7,776,615 B2 | 8/2010 | Yuka et al. |
| 8,182,768 B2 | 5/2012 | Tipler et al. |
| 8,342,042 B2 | 1/2013 | Scott et al. |
| 8,347,688 B2 | 1/2013 | O'brien |
| 8,388,736 B2 | 3/2013 | Marotta et al. |
| 8,404,185 B2 | 3/2013 | Tipler et al. |
| 8,465,700 B2 | 6/2013 | Huang |
| 8,561,484 B2 | 10/2013 | Tipler et al. |
| 9,329,066 B2 | 5/2016 | Skarping et al. |
| 9,404,900 B2 | 8/2016 | Herman et al. |
| 9,733,225 B2 | 8/2017 | Armstrong |
| 9,918,661 B2 | 3/2018 | Cormier et al. |
| 10,502,664 B2 | 12/2019 | Cardin |
| 10,835,155 B2 | 11/2020 | Phillips |
| 10,849,600 B2 | 12/2020 | Cardin |
| 10,866,166 B2 | 12/2020 | Shaikh et al. |
| 2002/0020209 A1 | 2/2002 | Grob et al. |
| 2002/0144949 A1 | 10/2002 | Berger et al. |
| 2003/0190757 A1 | 10/2003 | Furuno et al. |
| 2004/0072375 A1 | 4/2004 | Gjerde et al. |
| 2005/0014156 A1 | 1/2005 | Pawliszyn |
| 2005/0019950 A1 | 1/2005 | Gierde et al. |
| 2005/0233085 A1 | 10/2005 | Miller et al. |
| 2006/0073538 A1 | 4/2006 | Konrad |
| 2006/0137432 A1 | 6/2006 | Kin et al. |
| 2006/0286606 A1 | 12/2006 | Oliver |
| 2007/0193871 A1 | 8/2007 | Wiseman et al. |
| 2007/0284523 A1 | 12/2007 | May et al. |
| 2008/0009761 A1 | 1/2008 | Acker et al. |
| 2008/0064115 A1 | 3/2008 | Hiramatsu et al. |
| 2008/0179252 A1 | 7/2008 | Sasano et al. |
| 2009/0038374 A1 | 2/2009 | Broz |
| 2009/0317916 A1 | 12/2009 | Ewing et al. |
| 2010/0242579 A1 | 9/2010 | Tipler et al. |
| 2011/0033949 A1 | 2/2011 | Eum |
| 2011/0079143 A1 | 4/2011 | Marotta et al. |
| 2011/0082380 A1* | 4/2011 | Breen ............... A61M 16/0866 128/203.12 |
| 2011/0277563 A1 | 11/2011 | Scott et al. |
| 2012/0160038 A1 | 6/2012 | Wells et al. |
| 2012/0310113 A1 | 12/2012 | Giddings et al. |
| 2013/0017545 A1 | 1/2013 | Yong et al. |
| 2014/0060331 A1 | 3/2014 | Peene et al. |
| 2014/0329705 A1 | 11/2014 | Wong et al. |
| 2014/0345365 A1 | 11/2014 | Aono et al. |
| 2015/0005657 A1* | 1/2015 | Nijsen ................. A61M 16/085 600/543 |
| 2015/0075300 A1 | 3/2015 | Hankemeier et al. |
| 2015/0276780 A1 | 10/2015 | Bremer et al. |
| 2015/0364310 A1 | 12/2015 | Musselman |
| 2016/0189945 A1 | 6/2016 | Zhang et al. |
| 2017/0030892 A1* | 2/2017 | Fu ......................... G01N 33/64 |
| 2017/0261408 A1 | 9/2017 | Cardin |
| 2017/0284978 A1 | 10/2017 | Cardin |
| 2017/0303900 A1 | 10/2017 | Cardin |
| 2018/0246071 A1 | 8/2018 | Cardin |
| 2020/0041469 A1 | 2/2020 | Cardin |
| 2020/0191686 A1 | 6/2020 | Cardin |
| 2021/0396629 A1 | 12/2021 | Cognon et al. |
| 2022/0381766 A1 | 12/2022 | Cardin |

FOREIGN PATENT DOCUMENTS

| | | |
|---|---|---|
| CN | 202748263 U | 2/2013 |
| CN | 202748340 U | 2/2013 |
| CN | 203324233 U | 12/2013 |
| CN | 104133031 A | 11/2014 |
| CN | 104458970 A | 3/2015 |
| CN | 104698064 A | 6/2015 |
| CN | 105251238 A | 1/2016 |
| CN | 105510090 A | 4/2016 |
| CN | 105866272 A | 8/2016 |
| CN | 106124255 A | 11/2016 |
| CN | 107085046 A | 8/2017 |
| CN | 108693261 A | 10/2018 |
| CN | 109406231 A | 3/2019 |
| EP | 0572968 A2 | 12/1993 |
| EP | 2158469 A2 | 3/2010 |
| EP | 2469261 A1 | 6/2012 |
| EP | 2485035 A2 | 8/2012 |
| EP | 3040721 A1 | 7/2016 |
| JP | 5-506715 A | 9/1993 |
| JP | H08-160024 A | 6/1996 |
| JP | 10-185890 A | 7/1998 |
| JP | 2000-2695 A | 1/2000 |
| JP | 2002-236079 A | 8/2002 |
| JP | 2002328078 A | 11/2002 |
| JP | 2004-53268 A | 2/2004 |
| JP | 2005-510708 A | 4/2005 |
| JP | 2005-338081 A | 12/2005 |
| JP | 2007-514149 A | 5/2007 |
| JP | 2008-111730 A | 5/2008 |
| JP | 2010-96665 A | 4/2010 |
| JP | 2015-197444 A | 11/2015 |
| JP | 2016-126013 A | 7/2016 |
| JP | 2019-508718 A | 3/2019 |
| KR | 2004 0012068 A | 2/2004 |
| RU | 2085907 C1 | 7/1997 |
| RU | 34739 U1 | 12/2003 |

(56) References Cited

FOREIGN PATENT DOCUMENTS

| | | |
|---|---|---|
| SU | 817583 A1 | 3/1981 |
| WO | 1991/015745 A1 | 10/1991 |
| WO | WO09428409 A2 | 12/1994 |
| WO | 2002/086488 A1 | 10/2002 |
| WO | 2005/057206 A1 | 6/2005 |
| WO | WO2008020416 A2 | 2/2008 |
| WO | WO2008157074 A2 | 12/2008 |
| WO | 2008/157074 A3 | 1/2010 |
| WO | 2011/031559 A1 | 3/2011 |
| WO | WO2011143349 A1 | 11/2011 |
| WO | 2016/107515 A1 | 7/2016 |
| WO | WO2017156005 A1 | 9/2017 |
| WO | WO2018013946 A1 | 1/2018 |
| WO | 2018/160757 A1 | 9/2018 |

OTHER PUBLICATIONS

Notice of Allowance received for U.S. Appl. No. 15/649,480, dated Jul. 24, 2020, 11 pages.
Corrected Notice of Allowance received for U.S. Appl. No. 15/450,236, dated Nov. 13, 2019, 2 pages.
Dyne, et al., "A Novel Device for Capturing Breath Samples for Solvent Analysis", Science of the Total Environment, vol. 199, No. 1-2, 1997, pp. 83-89.
Final Office Action received for U.S. Appl. No. 15/649,480, dated Mar. 24, 2020, 9 pages.
International Search Report received for PCT Patent Application No. PCT/US2019/020995, dated Jun. 11, 2019, 4 pages.
Non-Final Office Action received for U.S. Appl. No. 15/649,480, dated Aug. 21, 2019, 18 pages.
Non-Final Office Action received for U.S. Appl. No. 15/908,491, dated Mar. 23, 2020, 12 pages.
Notice of Allowance received for U.S. Appl. No. 15/450,236, dated Jun. 20, 2019, 8 pages.
Restriction Requirement received for U.S. Appl. No. 15/908,491, dated Nov. 19, 2019, 7 pages.
Schubert, et al., "C02-controlled Sampling of Alveolar Gas in Mechanically Ventilated Patients", J. Appl Physiol, vol. 90, No. 2, 2001, pp. 486-492.
International Search Report received for PCT Patent Application No. PCT/US2019/044252, dated Nov. 11, 2019, 4 pages.
Non-Final Office Action received for U.S. Appl. No. 16/526,838, dated Jun. 13, 2022, 10 Pages.
Restriction Requirement received for U.S. Appl. No. 16/526,838, dated Mar. 9, 2022, 6 pages.
Anonymous, "Merlin MicroSeal Septumless GC Inlet Systems", Available online at: < https://www.hrgc.eu/merlin_microseal_introduction.htm>, retrieved on Oct. 31, 2019, 2014, pp. 1-4.
Entech Instruments, "Air Monitoring Sorbent Pens For Environmental and IH Applications", Available online at: <https://www.chimicacentro.itcataloghiEntech.Sorbent.Pens.pdf>, retrieved on Oct. 31, 2019, Dec. 31, 2017, pp. 1-15.
Pocurull et al., "Introduction Of Large Volumes Of Water-containing Samples Into A Gas Chromatograph", Journal Of Chromatography A, vol. 876, No. 1-2, Apr. 21, 2000, pp. 135-145.
Search Report Received for Chinese Patent Application No. 201980051020.2 dated May 7, 2022, 8 Pages (4 Pages of English Translation).
Non-Final Office Action received for U.S. Appl. No. 15/908,491, dated Dec. 4, 2020, 7 pages.
Search Report received for Chinese Patent Application No. 201780026386.5, dated Feb. 3, 2021, 4 pages (2 page of English Translation).
International Search Report dated Jun. 1, 2017, for PCT Application No. PCT/US2017/021167, seven pages.
International Search Report dated May 28, 2018, for PCT Application No. PCT/US2018/020313, six pages.
International Search Report dated Sep. 14, 2017, for PCT Application No. PCT/US2017/042172, six pages.
Non-Final Office Action dated Feb. 7, 2019, for U.S. Appl. No. 15/450,236, filed Mar. 6, 2017, 15 pages.
Advisory Action received for U.S. Appl. No. 16/526,838, dated Mar. 15, 2023, 2 pages.
Final Office Action received for U.S. Appl. No. 16/526,838, dated Aug. 31, 2023, 10 pages.
Final Office Action received for U.S. Appl. No. 16/526,838, dated Dec. 19, 2022, 9 pages.
International Search Report received for PCT Patent Application No. PCT/US2022/072637, dated Nov. 3, 2022, 7 pages.
Non-Final Office Action received for U.S. Appl. No. 16/526,838, dated May 25, 2023, 9 pages.
Non-Final Office Action received for U.S. Appl. No. 16/706,603, dated Aug. 18, 2022, 15 pages.
Hermann et al., "CGC Using A Programmable Electronic Pressure Controller", Journal of High Resolution Chromatography, vol. 13, No. 5, May 1990, pp. 361-365.

* cited by examiner

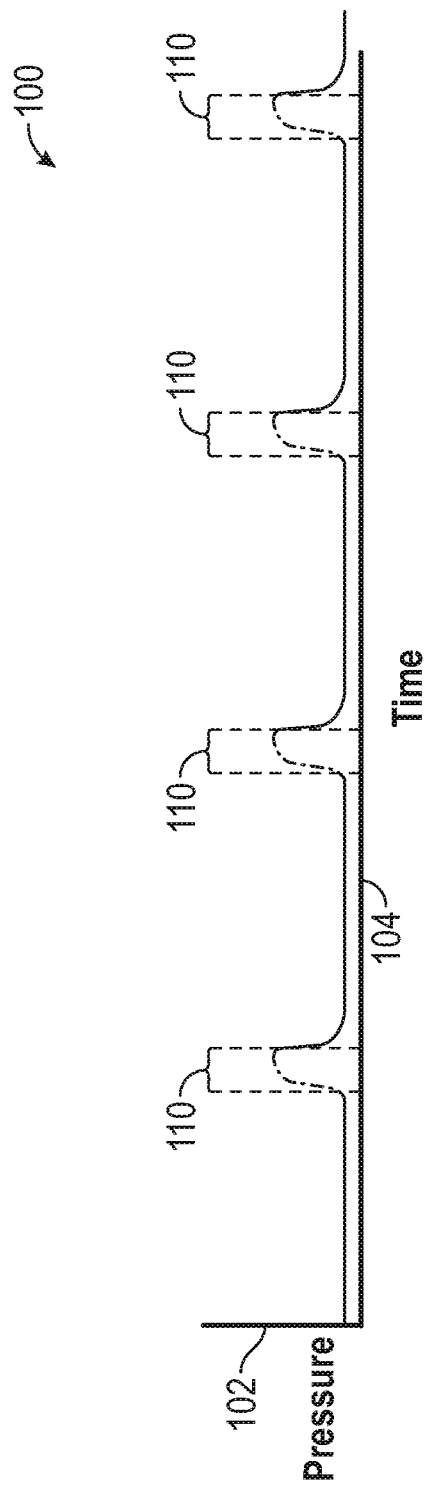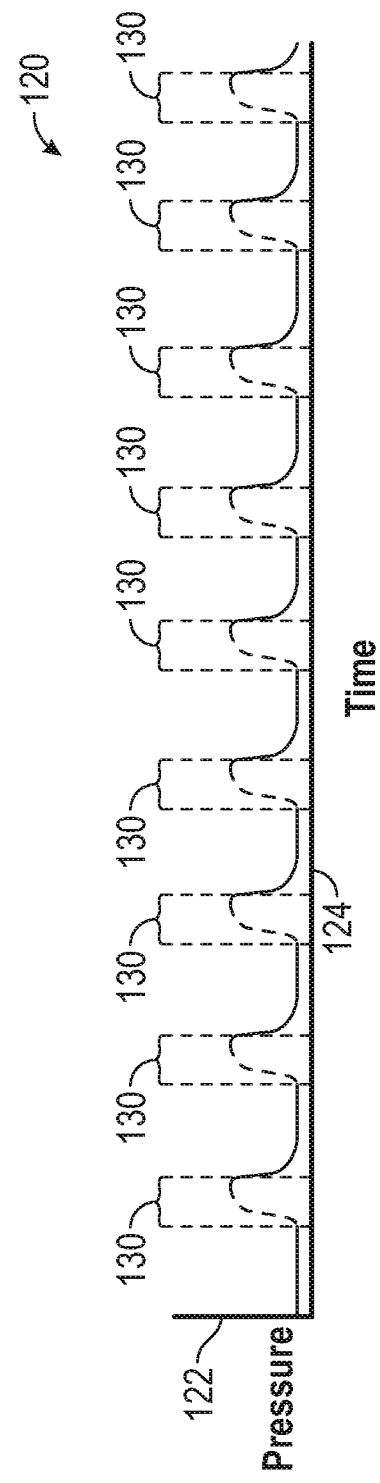

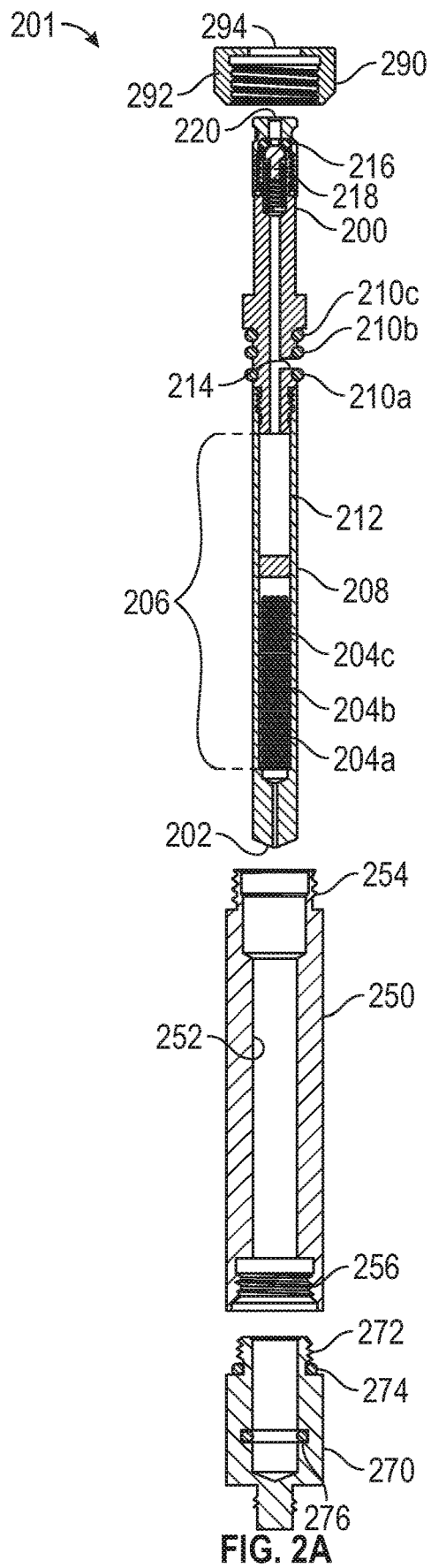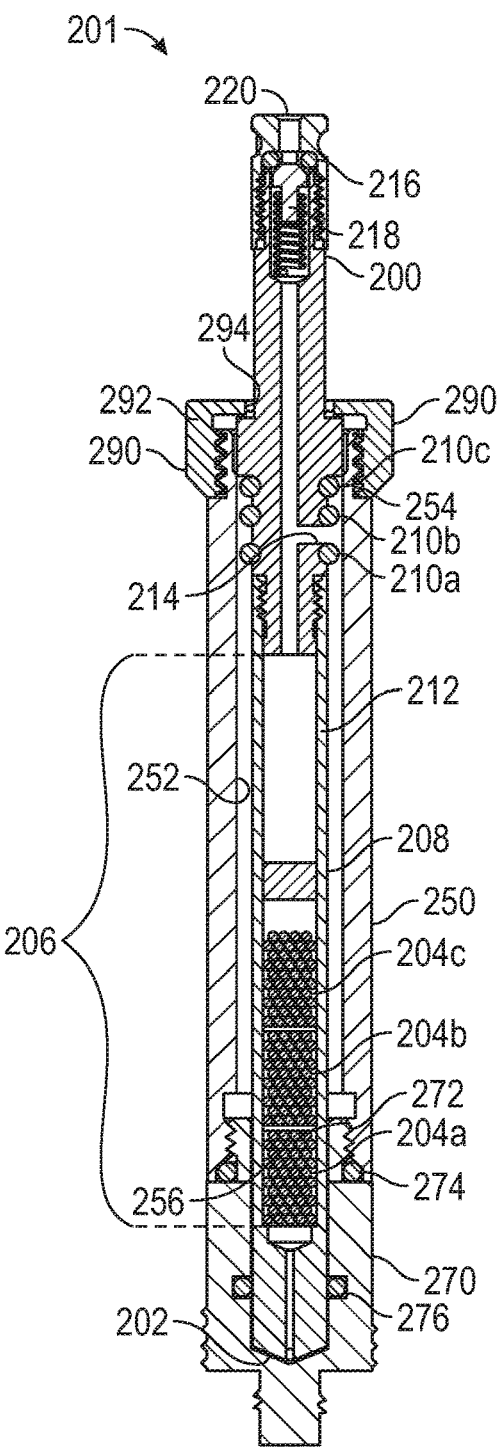
FIG. 2A
FIG. 2B

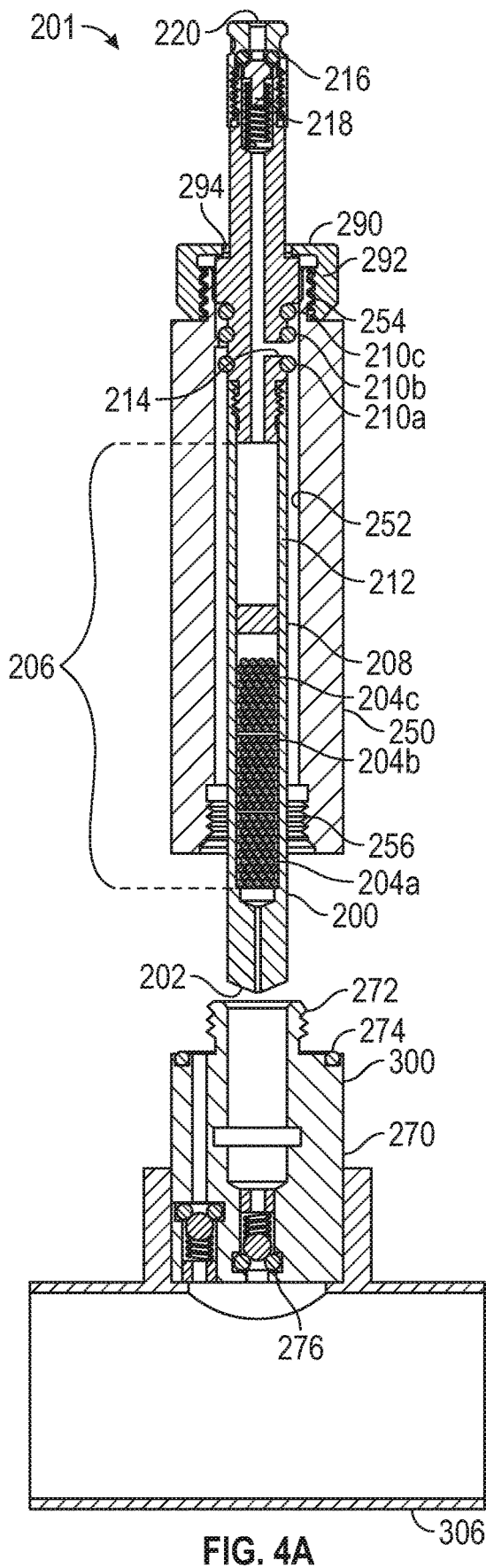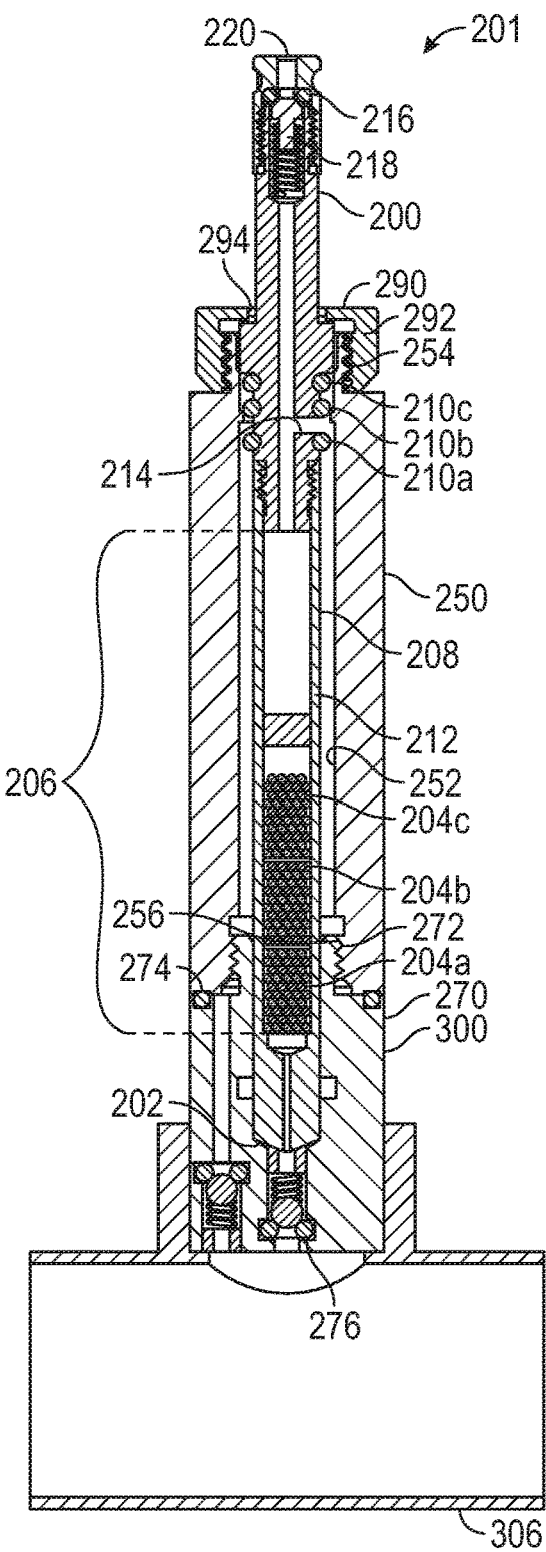
FIG. 4A
FIG. 4B

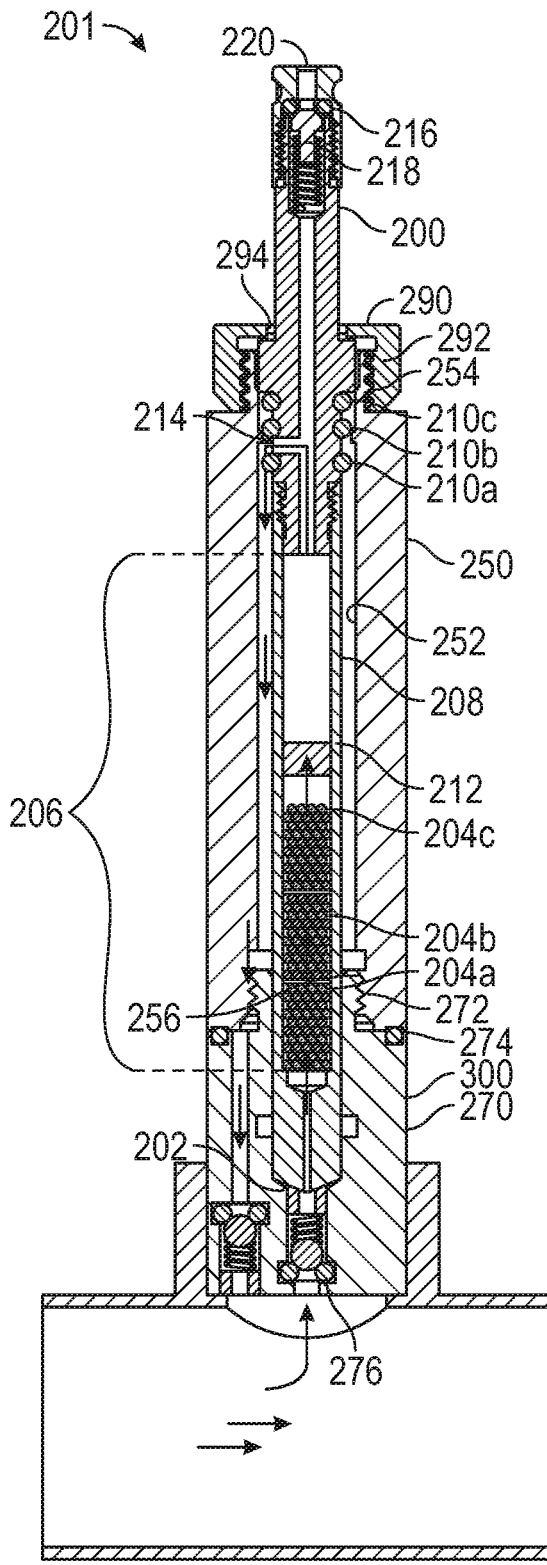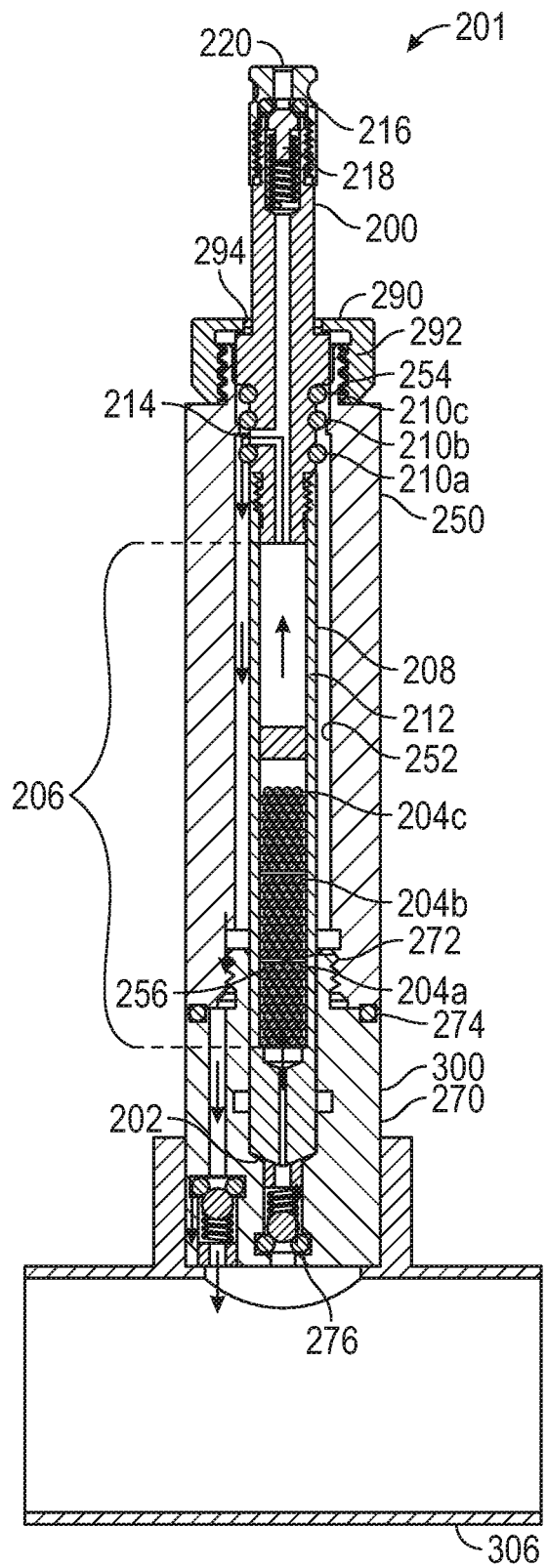
FIG. 5A
FIG. 5B

VENTILATOR-COUPLED SAMPLING DEVICE AND METHOD

CROSS-REFERENCE TO RELATED APPLICATIONS

This application claims priority to U.S. Provisional Patent Application Ser. No. 62/639,479, filed Mar. 6, 2018, entitled "VENTILATOR-COUPLED SAMPLE COLLECTION AND CHEMICAL ANALYSIS DEVICE AND METHOD," the content of which is hereby incorporated by reference for all purposes.

FIELD OF THE DISCLOSURE

This relates to the collection of Volatile Organic Compounds in exhaled breath while monitoring patients on breathing assisted ventilators.

BACKGROUND

It has long been understood that breath contains a wide variety of chemicals that can indicate various metabolic or disease states within the human body. Due to the complexity of breath and the hundreds or thousands of volatile compounds that can be found in the breath at low levels, accurate analyses can generally be done using equipment such as Gas Chromatography/Mass Spectrometry, or GCMS. These instruments are not small, and are not generally mobile. Therefore, GCMS analysis on human breath is generally performed by collecting the sample using either an adsorbent for thermal desorption or solvent extraction, or by using whole air techniques such as Tedlar bags or canisters. Solvent extracted sorbents and Tedlar bags, however, are generally effective at high PPB to PPM levels, and generally not effective for detecting compounds at sub-PPB levels. Vacuum canisters can allow multiple analyses to be performed as needed, and can be effective when the sample is to be pre-screened or analyzed multiple times. Thermal desorption tubes are generally less expensive than vacuum canisters, but are usually more complicated to perform sampling with because they require sampling pumps to meter in a known volume of sample, and a reliable power source. Canisters are evacuated prior to delivery to the sampling location, so just opening the valve will cause air and VOCs to flow into them. However, collecting a breath sample with canisters can also become more complicated when taking a time weighted average sample over minutes or hours due to the use of flow restrictors or controllers.

SUMMARY

This relates to the collection of Volatile Organic Compounds in exhaled breath while monitoring patients on breathing assisted ventilators. The concentration and types of VOCs can be used to diagnose disease and infection in the lungs, such as with bacterial infections, as well as providing marker chemicals that can indicate a host of other diseases or infections. In some embodiments, a tube is connected to the outlet line of the ventilator, near a location of the outlet line where the ventilator line connects into the control unit. Upon exhalation, the air remaining in the outlet line can include deep, alveolar air from deep within the lungs that can contain rich levels of VOCs.

As the ventilator unit pressurizes the inlet line during inspiration, both the inlet line and outlet line can pressurize. As a result, the outlet line compresses and pressurizes the previously-exhaled breath remaining in the outlet line. This pressurization can be used to drive a small amount of the compressed exhaled air through an adsorbent by opening a one-way valve to allow air to flow into the adsorbent. In this way, the exhaled air can be sampled without the use of an additional pump other than the ventilator pump that drives the pressurization of the ventilator lines. Approximately 0.015 to 1 cc per inhaled breath, or about 0.2 to 12 cc/min for an average 12 breath cycles per minute, can enter the sample collection device during a sampling process.

A sleeve can be placed around the adsorbent device and an outlet at the end of the adsorbent device can allow air to fill into this sleeve volume after passing through the adsorbent, thereby increasing the amount of air sampled through the adsorbent during each pressurization cycle, for example. The sleeve volume can be coupled to another one-way valve that allows the air to release back into the ventilator line once the VOCs have been extracted.

Sampling for an hour using 15 cm H2O pressure during each pressurization cycle can enable the system to collect between 18 to 720 cc of air per hour, for example. In some embodiments, this amount is adjustable based on changing the volume added by the outer sleeve or an optional inlet reservoir. Collecting between 18 and 720 cc of air per hour can allow detection of VOCs down to sub-PPB levels or even down to low part-per-trillion levels if a preconcentration and splitless injection is performed into a GCMS. Hundreds of different VOCs can be monitored to determine levels of infection, levels of various disease markers, and levels of anesthesia in the breath. The device can be easy to implement and use. Hospital staff can unscrew a cap and screw or click the adsorbent onto a tee connector to attach the sampling device to the ventilator line. Thus, hospital staff can perform the sample collection with minimal training and the analysis can be performed in a nearby lab using GC or GCMS.

It has long been desired to reduce the complexity of tube sampling, and one approach has been to use diffusion tubes that will adsorb compounds at a constant rate during the exposure period. Diffusive sampling onto thermal desorption tubes without the need for a pumping mechanism can also collect and enrich VOCs prior to GC or GCMS analysis. Diffusive sampling rates for many VOCs have been determined using diffusive tubes having a 5 mm opening and a depth of 15 mm to the start of the adsorbent bed, such as the tubes described in US EPA Method 325. Unfortunately, diffusive sampling tubes can have a limited range of compounds that they can collect, for example, because the sorbent needs to be strong enough to irreversibly adsorb the compounds of interest at the sampling temperature yet must completely release all compounds during analysis at a desorption temperature that is higher than the sampling temperature. Generally, different adsorbents are used to collect each of C3-C6 compounds, C4-C8 compounds, and C6-C12 compounds using diffusive tubes. Therefore, a simple yet active sampling solution for collection of ventilator air onto a thermal desorption tube is needed to maximize the range of compounds that can be recovered so that a superior solution for monitoring of disease indicating VOCs can be achieved. Such a solution is presented here.

BRIEF DESCRIPTION OF THE DRAWINGS

FIGS. 1A-1B illustrate exemplary pressurization patterns for ventilators according to some embodiments of the disclosure.

FIGS. 2A-2B illustrate a sample collection system according to some embodiments of the disclosure.

FIGS. 4A-4B illustrate the sample collection system coupled to the ventilator outlet line according to some embodiments of the disclosure.

FIGS. 5A-5C illustrate the flow of air in the sample collection system during a sampling process according to some embodiments of the disclosure.

DETAILED DESCRIPTION

Figure 3A:
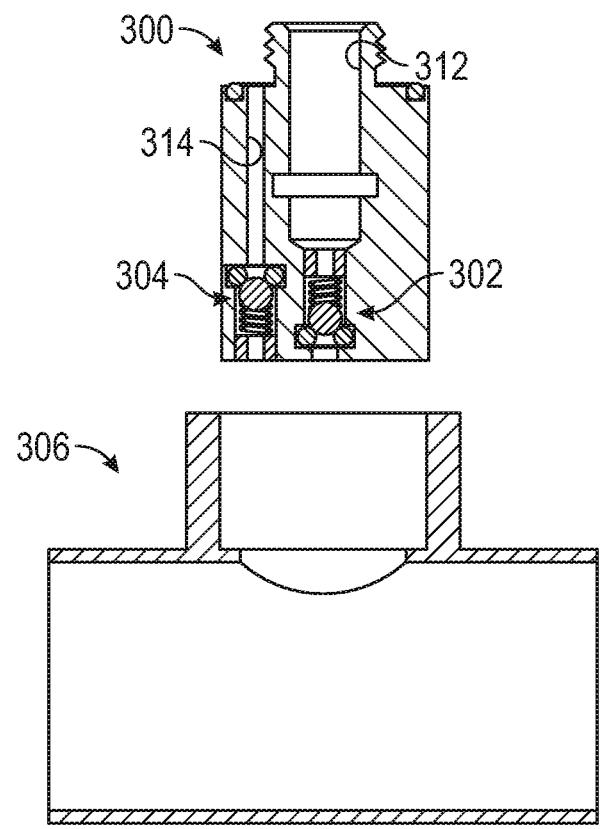
FIGS. 3A-3B illustrate coupling that connects the sample collection device to the ventilator outlet line according to some embodiments of the disclosure.

The disclosed system and methods use active sampling onto single or multi-bed adsorbent traps, but are as straightforward as systems and methods that use diffusive tubes, as no costly calibrated pump or power source in addition to the components of the ventilator itself are needed, for example. The disclosed system takes advantage of the accurate regulation of ventilators in use today, which can consistently reproduce pressures and pulse times during each breathing cycle. By actively flowing through the adsorbent, multiple adsorbent beds can be used to capture and release a wider volatility range of VOCs. Increasing or maximizing both sensitivity and recovery of the widest possible volatility range of compounds, which this technique achieves, is important as it is not currently known which chemicals are the most important to monitor.

In some embodiments, sample is collected for a monitoring period of 30 minutes to an hour. A shorter period may not allow sampling of a large enough volume to reach required detection limits, for example. Because the pressurization of ventilators is generally about 15 cm H2O (15 mBar), or about 1.5% of atmospheric pressure, a 3-8 cc combined internal volume constitutes about 0.045-0.12 cc per inspiration/exhalation cycle. Sampling at slow rates can improve the recovery of chemicals as it allows them to adsorb close to the front of the adsorbent bed. Over a period of 30-60 minutes, a total volume of 5-500 cc can be collected, depending on the total internal volume of the sample collection device, which can result in low detection limits. The sample collection device can be heated to a temperature slightly above the patient's body temperature to prevent the relative humidity within the sample collection device from reaching 100%. A low-wattage (e.g., 2-3 watts) heater can heat the sample collection device to avoid condensing conditions. The collection of 200 cc or less can allow management of water condensation using the appropriate thermal desorption systems without having to apply gentle heating to the sample collection device, with special attention paid to the construction of the one-way valves (e.g., check valves) to avoid clogging the valves with liquid water if a heater is not used.

FIGS. 1A-1B illustrate exemplary pressurization patterns for ventilators according to some embodiments of the disclosure. Ventilators can operate in several modes of operation. Thus, the operation mode and its corresponding pressurization pattern is taken into account when determining how much sample will pass through the adsorbent device during the sampling period. As long as the average number of cycles per minute is known, the volume collected can be determined by the formula:

$$(\text{Volume of Tube, Sleeve, and Reservoir}) \times (\text{Average cycles per minute}) \times (\text{sampling period in minutes}) \times (P1-P2)/Pa$$

Where P1 is the pressure used during inspiration and P2 is the exhale pressure and Pa is atmospheric pressure. The tube, sleeve, and reservoir and their associated volumes will be described in more detail below with reference to FIGS. 2A-6C.

FIG. 1A illustrates an exemplary pressurization pattern 100 for a ventilator operating in a control mode. In the control mode, breaths are generally initiated by the ventilator. The pressurization pattern 100 illustrates the pressure 102 of the ventilator lines over time 104. As shown in FIG. 1A, during inspiration 110, the pressure 102 in the ventilator lines rises. After inspiration 110 is complete, the pressure 102 in the ventilator lines is allowed to decrease. Inspiration 110 corresponds with a controlled inhale. After inhalation, the patient exhales as the ventilator pressure is reduced.

FIG. 1B illustrates an exemplary pressurization pattern 120 for a ventilator operating in an assist mode. In the assist mode, breaths are generally initiated by the patient. The pressurization pattern 120 illustrates the pressure 122 of the ventilator lines over time 124. As shown in FIG. 1B, during inspiration 130, the pressure 122 in the ventilator lines rises. After inspiration 130 is complete, the pressure 122 in the ventilator lines is allowed to decrease. Inspiration 130 corresponds with a controlled inhale. After inhalation, the patient exhales as the ventilator pressure is reduced.

FIGS. 2A-2B illustrate a sample collection system 201 according to some embodiments of the disclosure. The sample collection system 201 can include a sample collection device 200, a sleeve 250, and caps 270 and 290.

The sample collection device can include a sampling inlet 202. The inlet 202 can be narrow enough to prevent backward diffusion (e.g., diffusion of compounds from the sorbent to the inlet of the sample collection device) during slow active sampling, and to decrease the component of positive diffusive sampling to nearly zero. As discussed above, ¼" TD tubes with a 5 mm opening can sample diffusively at up to 0.7 cc/min, so active sampling at only 1-3 cc/min as obtained with ¼" TD tubes would include a diffusive component when using standard thermal desorption tube inlet diameters of about 5 mm. With the disclosed approach, the diffusive sampling component is virtually zero because of the narrow inlet diameter. The inlet diameter can be as low as 0.031 inches and the outer diameter of the cavity 206 of the sample collection device 200 is in the range of ⅛" to ⅜" and the inner diameter of the cavity 206 of the sample collection device 200 can be less than the outer diameter, such as 0.062" to 0.34" (e.g., 0.195 inches or 5 mm).

The sample collection device further includes one or more sorbents 204. The total amount of sorbent used can be in the range of 50-500 mg, with one to three kinds of sorbents 204. When using multiple kinds of sorbents 204 with increasing strength, the sorbents 204 can be separated from one another by screens that prevent mixing of the sorbents. For example, the sample collection device includes three sorbent beds 204a, 204b, and 204c to increase the compound volatility range that can be recovered. The total overall length of the sorbent beds 204 is around 0.8 to 1.5 inches, with the length of the sample collection device 200 being around 3.5 to 4.5 inches. The bed 204a closest to the inlet 202 can have the lowest chemical affinity to the one or more target compounds, while the last bed 204c can have the greatest chemical affinity to the one or more target compounds. In other words, the sorbent bed 204a closest to the inlet 202 is the "weak" or "weakest" sorbent while the sorbent bed 204c furthest from the inlet 202 is the "strong" or "strongest" sorbent. In some examples, the sample collection device 200 includes another sorbent bed 204b between the weak sorbent bed 204a and the strong sorbent bed 204c that can have a chemical affinity for the one or more target compounds that is between the chemical affinities of the other sorbent beds 204a and 204c. As an example, the first sorbent bed 204a includes 5-40 $m^2$/g of Tenax, Tenax TA, Carbopack C or a similar sorbent, the second sorbent bed 204b includes 30-200 $m^2$/g of Tenax TA, Carbopack B or a similar sorbent, and the third sorbent bed 204c includes 200-1200 $m^2$/g of Carbopack X, Carboxen 1000, Carbon Molecular Sieves, or a similar sorbent. Carbopack C, B, X, and Carboxen 1000 are registered trademarks of Supelco (now Sigma Aldrich/Millipore) in Pennsylvania, United States of America. During analysis, the cavity 206 of the sample collection device 200 can be heated and back flushed to prevent the heavy compounds from reaching the strong sorbent 204c or sorbents (e.g., compounds trapped in sorbent bed 204a do not reach sorbent bed 204b or sorbent bed 204c).

The sample collection device 200 can include a retaining frit 208. The retaining frit 208 retains the sorbent beds 204 in place. It can be advantageous for the sorbents 204 to remain proximate to the opening 202 of the sample collection device 200, thus the retaining frit 208 can be used to retain the sorbents in the position illustrated. By positioning the sorbents 204 away from external seals 210, the sorbents 204 can be heated to a high desorption temperature during desorption while a heat sink (not shown) placed near the external seals 210 can prevent the seals from being damaged due to the high heat.

The sample collection device includes an internal volume 212. Volume 212 is the space in cavity 206 not occupied by the sorbent 204. Volume 212 can be either filled with an inert material such as glass beads, a glass rod, or other inert, low thermal conducting material, or kept open to maximize the unoccupied volume. Volume 212 can create space between the sorbent and the seals, which can be advantageous for the reasons discussed above. During sampling, as will be described in more detail below, the volume 212 can hold air that has passed through the sorbent 204. Increasing the internal volume of the sample collection system 201 can increase the volume of air that can be sampled during a sampling period of known duration (e.g., an hour).

The sample collection device further includes a port 214. The port 214 can be located between two of the external seals 210a and 210b (e.g., the port is between the two lowest of three seals). During sampling, the port 214 allows gas that has passed through the adsorbent to exit the cavity 206 of the sample collection device 200 and flow into the inside 252 of the outer sleeve 250, as will be described in more detail below. During analysis, the port 214 is used to supply a carrier fluid (e.g., a carrier gas) to back desorb the sorbent 204 during GC or GCMS analysis. The seals 210 isolate the tube during the travel, such as between the sample collection site (e.g., the ventilator) and the sample analysis site (e.g., a lab). It also prevents leakage during pressurization. Sample collection device 200 further includes an internal seal 216 and valve 218 that seal a top opening 220 during sample collection, transport, and desorption. During sampling, a pressure sensor (not shown) or a balloon (see FIGS. 7A-8B) or other elastic, expandable device can be attached to the sample collection device 200 at the valve 218 end to indicate the change in pressure in the sample collection device 200, which indicates that sampling is occurring. In some embodiments, sample collection device 200 does not include internal seal 216, valve 218, and top opening 220 and instead is closed at the top.

The sleeve 250 can function to isolate the sample collection device 200 when the sample collection device 200 is not in use. The sleeve 250 includes an internal volume 252, threads 254 and threads 256. The sample collection device 200 can be placed into sleeve 200, and cap 290 screws down onto the sleeve 200 at threads 254 to retain the sample collection device 200 within the sleeve 260 until returned to the lab. Cap 290 includes threads 292 that couple to the threads 254 of the sleeve and an opening 294 that allows the top part of the sample collection device 200 to pass through the cap 290 when the cap 290 and sleeve 270 are assembled, as shown in FIG. 2B.

During sampling, the port 214 of the sample collection device 200 is open to the internal volume 252 of the sleeve 250, as will be described in more detail below. When the sample collection device 200 is not in use, isolation cap 270 can be screwed on to the sleeve 250 at threads 256 to keep the sorbent 204 isolated both before and after sampling. Isolation cap 270 includes threads 272, external seal 274, and internal seal 276. Threads 272 can be coupled to the threads 256 of sleeve 250. External seal 274 forms a seal between the isolation cap 270 and the sleeve 250 when the isolation cap 270 is attached to the sleeve 250. Internal seal 276 provides additional sealing of the inlet 202 of the sample collection device 200.

FIG. 2B illustrates the sample collection system 201 with the sample collection device 200 fully isolated from its external environment. As shown in FIG. 2B, cap 290 can be screwed onto sleeve 250 at one end of the sample collection device 200 and cap 270 can be screwed onto sleeve 250 at the other end of the sample collection device 200. When assembled in this way, cap 290 is fitted around the sample collection device 200. The sorbent 204 of the sample collection device 200 is sealed from the external environment by the caps 290 and 270 and internal seal 216.

Figure 3B:
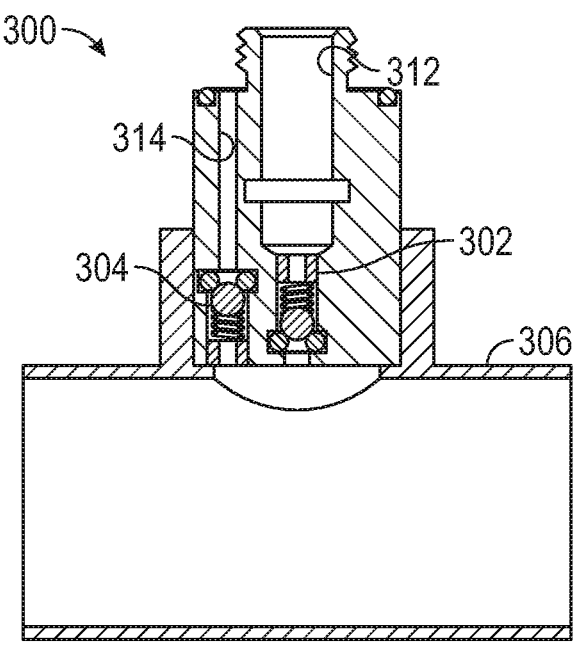

FIGS. 3A-3B illustrate coupling 300 that connects the sample collection device 200 to the ventilator outlet line according to some embodiments of the disclosure. The coupling 300 includes an intake one-way valve 302 and an outlet one-way valve 304 (e.g., check valves). Thus, coupling 300 is a valve system. During sampling, the sample collection device 200 is connected to coupling 300 which connects to the ventilator outlet line at tee 306. The pressure differential rating of the one-way valves 302-304 can be set by the ventilator and/or the patient's needs or tolerances. The pressure differential of the ventilator cycle can be around 10-15 cm H2O (e.g., 0.14-0.21 psi). The one-way valve 302 can therefore open when the pressure differential from the ventilator outlet line into the sampler is a positive 0.02 to 0.1 psi, while the one-way valve 304 can open when the pressure is greater in the sampler relative to the ventilator outlet line by 0.02-0.1 psi between inspiration pulses.

During inhalation, air from the ventilator output line can flow into the sample collection device 200 through the intake one-way valve 302 of the coupling 300. Intake one-way valve 302 can allow selective opening and closing of inlet 312 of the coupling 300. The pressure in the ventilator outlet line, which is higher than the pressure in the sample collection device 200 during inhalation, can cause the intake one-way valve 302 to open. Once inside the sample collection system 201, the air can then flow through the sorbent 204 of the sample collection device 200, allowing the sorbent 204 to adsorb or absorb one or more VOCs present in the exhaled breath.

During exhalation, the air that has passed through the sorbent 204 can flow through the volume 252 of the sleeve 250 and back into the ventilator output line (e.g., through tee 306) through the outlet one-way valve 304 of the coupling. Outlet one-way valve 304 can allow selective opening and closing of the outlet 314 of the coupling 300. The pressure in the sample collection system 201, which is higher than the pressure in the sample collection device 200 during exhalation, can cause the outlet one-way valve 304 to open. Additional details of the sampling process and the airflow into and out of the sample collection device 200 will be described below.

FIGS. 4A-4B illustrate the sample collection system 201 coupled to the ventilator outlet line according to some embodiments of the disclosure. In some examples, the sample collection device 200 can be received by the hospital in the sleeve and cap assembly illustrated in FIG. 2B. FIG. 4A illustrates the sample collection device without a cap isolating the inlet 202 of the sample collection device 200. FIG. 4A also includes the coupling 300 for fitting the sample collection device to the ventilator outlet line via tee 306. The coupling 300 is sized to fit the inlet end of the sample collection device 200, enabling the sample collection device 200 to collect a sample from the ventilator outlet line once the sample collection device 200 is fitted into the coupling 300. The sample collection device 200 and the coupling 300 can be threadingly coupled.

FIG. 4B illustrates the sample collection device 200 coupled to the ventilator line by way of coupling 300 and tee 306. When the sample collection device 200 is connected to the coupling 300, sampling can begin. When sampling is done, the process is reversed by unscrewing the sample collection device 200, replacing the isolation cap 270, and then returning the sample collection device 200 in its cap and sleeve assembly to the laboratory for analysis.

Figure 5C:
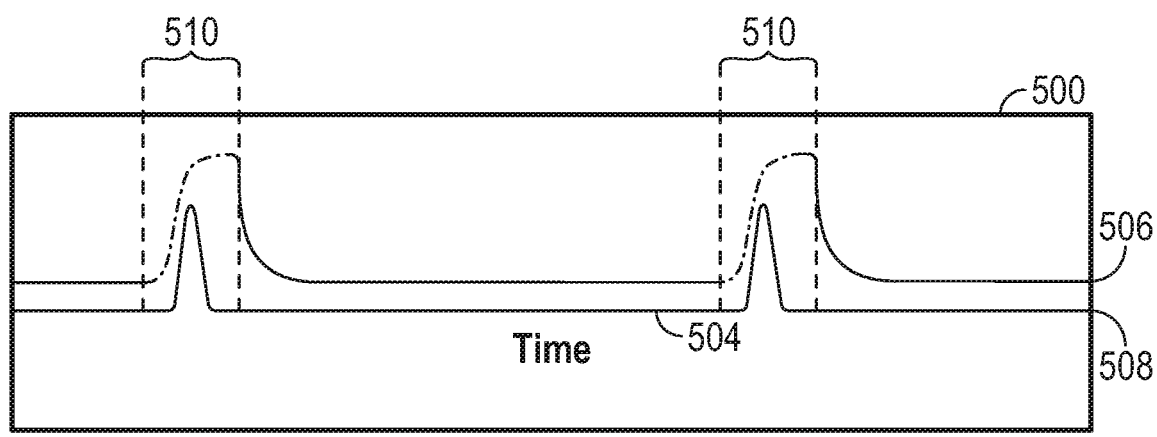

FIGS. 5A-5C illustrate the flow of air in the sample collection system 200 during a sampling process according to some embodiments of the disclosure. FIG. 5A illustrates airflow while inspiration (e.g., inhalation) is occurring, and the pressure is increasing by 10 to 20 cm H2O relative to expiration (e.g., exhalation), typically. The gas that is pressurized into the outlet line, and tee 306, is the deep alveolar air left from the end of the previous exhalation. As the pressure increases, the intake one-way valve 302 of coupling 300 allows flow into the inlet 202 of the sample collection device 200 and through the sorbent 204. VOCs are collected by the sorbent 204, and the air, which is not retained by the sorbent 204, continues through the sample collection device 200 where it reaches the port 214. The air continues to flow through the port 214 to the outside of the sample collection device 200 where it is now confined by the volume 252 of the outer sleeve 250. The gas continues to pressurize the rest of the volume down to the outlet one-way valve 304 of the coupling 300. However, while the pressure of the ventilator outlet line is pressurized during inspiration, the one way valve 304 does not allow flow out of the sample collection system 201, as the pressure is greater in the ventilator line than inside the sleeve 250.

FIG. 5B illustrates airflow through the sample collection system 201 during the exhalation stage of the cycle. The exhalation stage of the cycle is typically longer than the inspiration or pressurization stage. During exhalation, the pressure is higher inside the sample collection device 200 and its sleeve 250, so no flow can occur through the inlet one-way valve 302. Instead, the gases are drawn out through the back of the sample collection device 200 and into the outer sleeve 250 where it ultimately passes through the outlet one-way valve 304 and back into the ventilator outlet line through tee 306. Thus, air from the ventilator outlet line is drawn into and through the sample collection device 200 and, after sampling has occurred, back into the ventilator outlet line through tee 306 using the pressure cycle of the ventilator outlet line. The sample collection device 200 is able to collect the sample without including a pump that is separate from the pump included in the ventilator. The consistency of the ventilator and its ability to maintain a record of average cycles per minute, and often the number of total cycles during some monitoring period, allows this sampling strategy to be reliable and repeatable. When samples are not being collected, a blank sample collection device or a plug can be attached to coupling 300 to seal the ventilator outlet line. Alternatively, a sealing plunger/o-ring in the tee coupling can create an automatic seal upon removal of the sampling tube.

FIG. 5C illustrates a chart of the change in pressure 506 in the ventilator outlet line and the flow rate 508 of air into the sample collection device 200 during sampling over time 504 as illustrated in FIGS. 5A-5B. The pressure 506 in the ventilator outlet line increases during inspiration 510 and decreases during exhalation. During inspiration 510, flow into the sample collection device 200 occurs. Flow into the sample collection device 200 can occur during a period of time that is not as long as the ventilator inspiration stage 510, considering the limited volume of sample collection device 200. For ease of illustration, chart 500 includes indication of flow into the sample collection device 200 (e.g., illustrated in FIG. 5A) but does not include negative flow out of the sample collection device 200 (e.g., illustrated in FIG. 5B).

Figure 6A:
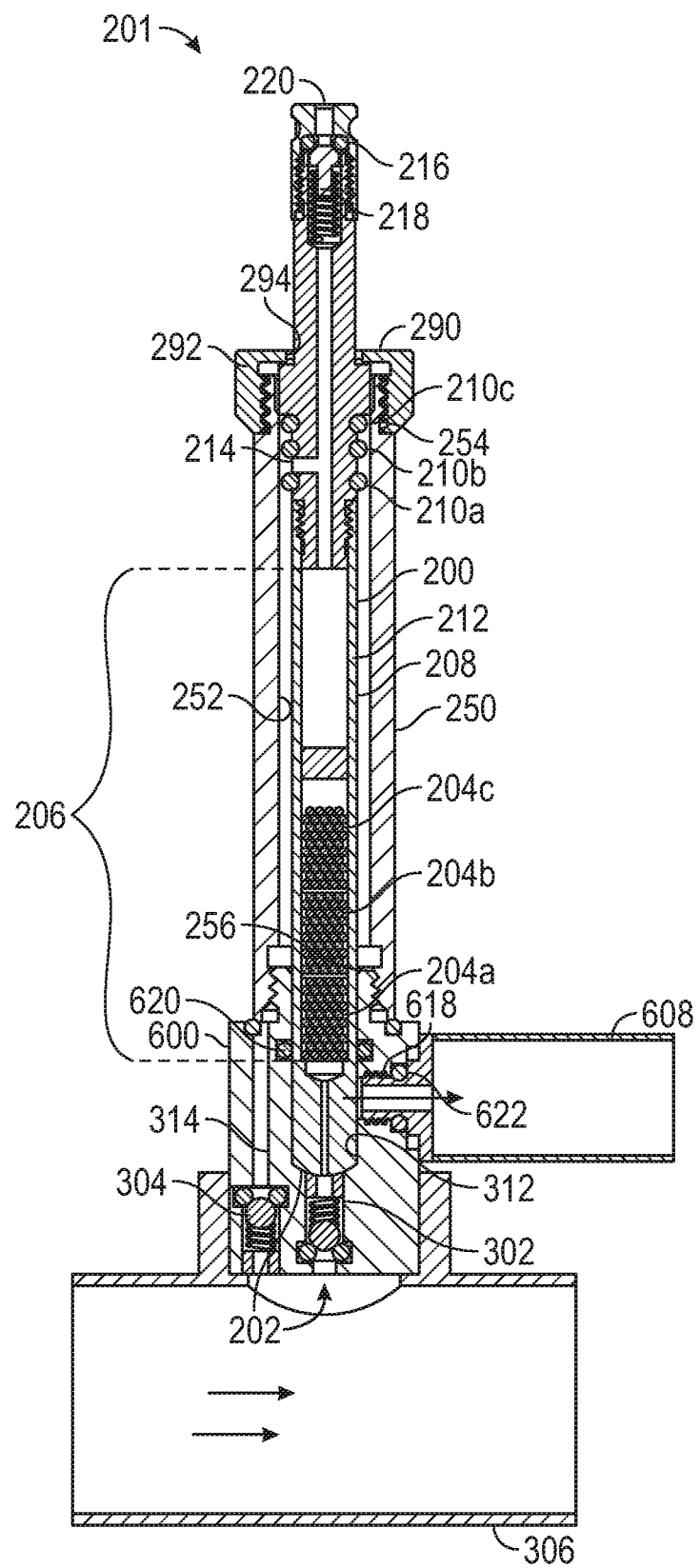
FIGS. 6A-6C illustrate airflow of another sample collection system during sampling according to some embodiments of the disclosure.
Figure 6B:
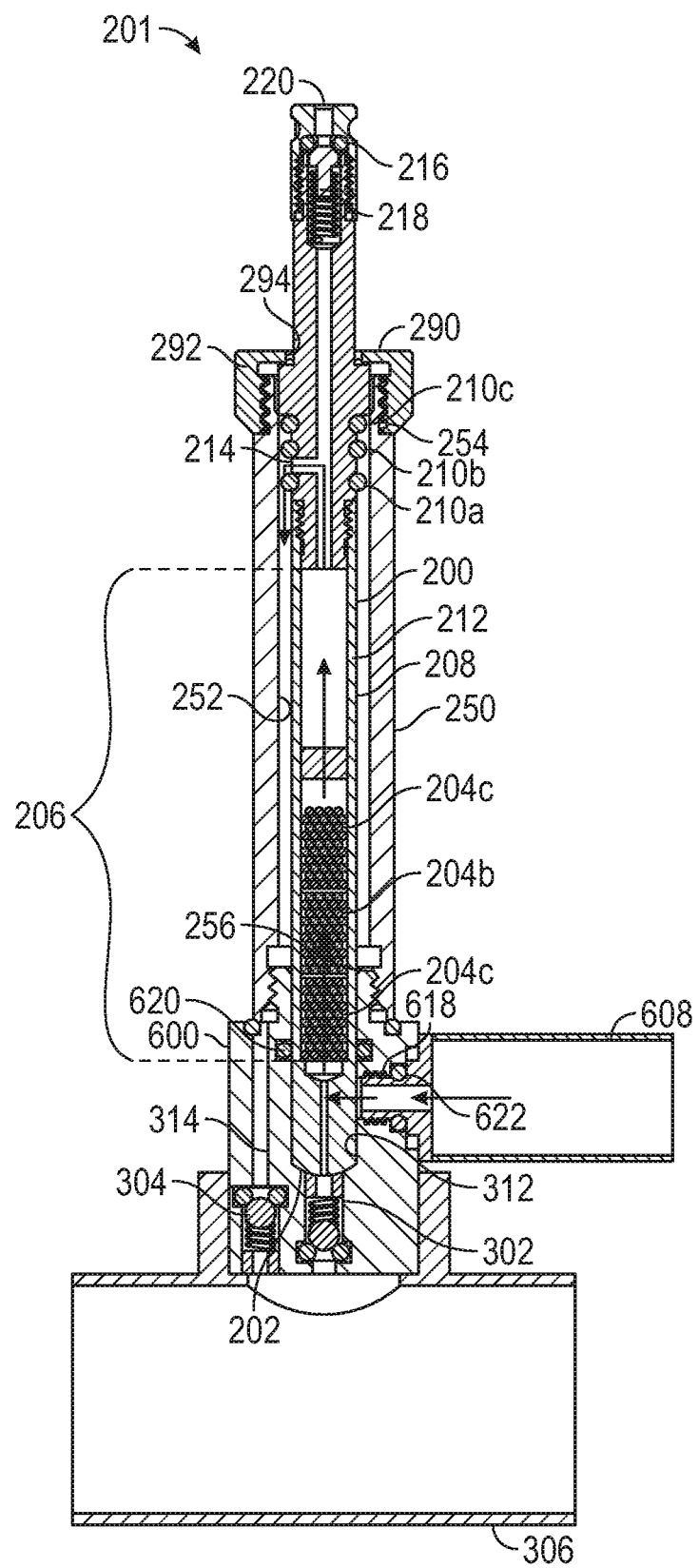
Figure 6C:
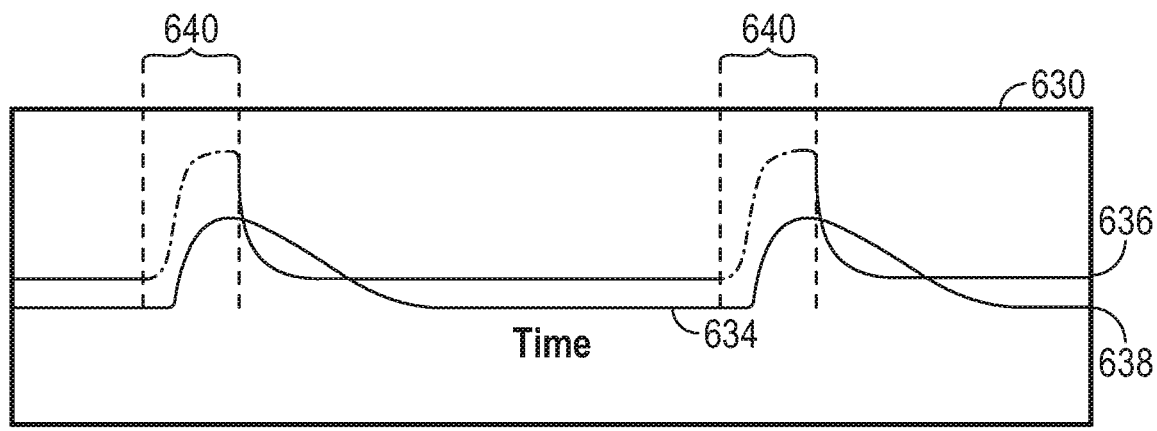

FIGS. 6A-6C illustrate airflow of another sample collection system during sampling according to some embodiments of the disclosure. Sample collection system includes the same components as the sample collection system described above with reference to FIGS. 2A-5C, with some exceptions noted here. Sample collection system includes a modified coupling 600 that includes a coupling to a reservoir 608. The reservoir has a volume of 1 to 100 cc (e.g., 3 to 10 cc). The coupling 600 to the reservoir 608 includes threads 618 around an opening at which to attach the reservoir 608 and a seal 622 to seal the connection between the coupling 600 and the reservoir 608. Coupling 600 further includes an additional seal 620 to seal the opening of sleeve 250 from the reservoir 608.

As shown in FIG. 6A, when the inspiration pulse occurs, the reservoir 608 fills with air that enters the sample collection system 201. The reservoir 608 can fill at a higher rate than the cavity 212 of sample collection device 200 because there is no sorbent impeding the flow into the reservoir 606, as there is in the case of flow into the cavity 212 of sample collection device 200 (e.g., sorbent 204).

As shown in FIG. 6B, after pressurization (e.g., during exhalation), the air can exit the reservoir 508 and flow through the adsorbent 204 and out the outlet one-way valve 304. In some embodiments, a restriction may be used at outlet 314 instead of a one-way valve 304. Since the recovery time is generally 2-4 times longer than the inspiration time, rapid filling of the reservoir 604 must be accomplished, but then flow through the adsorbent 204 may occur over that period where the pressure of the ventilator line is less than that of the reservoir 250 and sample collection device 200 assembly. Having one less valve may improve the long term reliability of the sample collection system 201. In this mode, having the assembly vertical or nearly vertical may allow any return spring in the outlet one-way valve 304 to be eliminated, just relying on gravity to close a ball against an o-ring, or some other light material over a port, for example. When samples are not being collected, a blank sample collection device or a plug can be attached to coupling 300 to seal the ventilator outlet line, or a plunger o-ring combination can automatically close the tee coupling when the sampling device 201 is removed.

FIG. 6C illustrates a chart of the change in pressure 636 in the ventilator outlet line and the flow rate 638 of air into the sample collection device 200 during sampling over time 634 as illustrated in FIGS. 6A-6B. The pressure 636 in the ventilator outlet line increases during inspiration 640 and decreases during exhalation. During inspiration 640, flow into the sample collection device 200 occurs. Flow into the sample collection device 200 can occur during a period of time that does not fully overlap with the ventilator inspiration stage 640 (e.g., flow into the sample collection device 200 can continue to occur after inspiration 640 has ceased). For ease of illustration, chart 630 includes indication of flow into the sample collection device 200 (e.g., illustrated in FIG. 6A) but does not include negative flow out of the sample collection device 200 (e.g., illustrated in FIG. 6B).

Figure 7A:
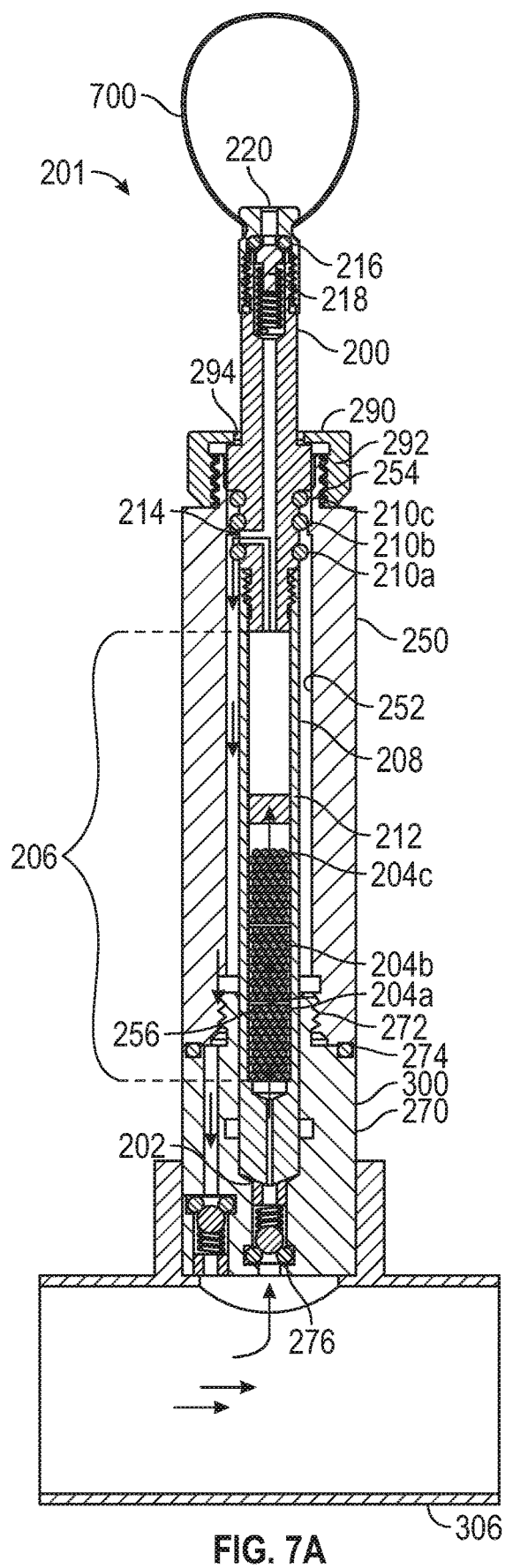
FIGS. 7A-7B illustrate another sample collection system according to some embodiments of the disclosure.
Figure 7B:
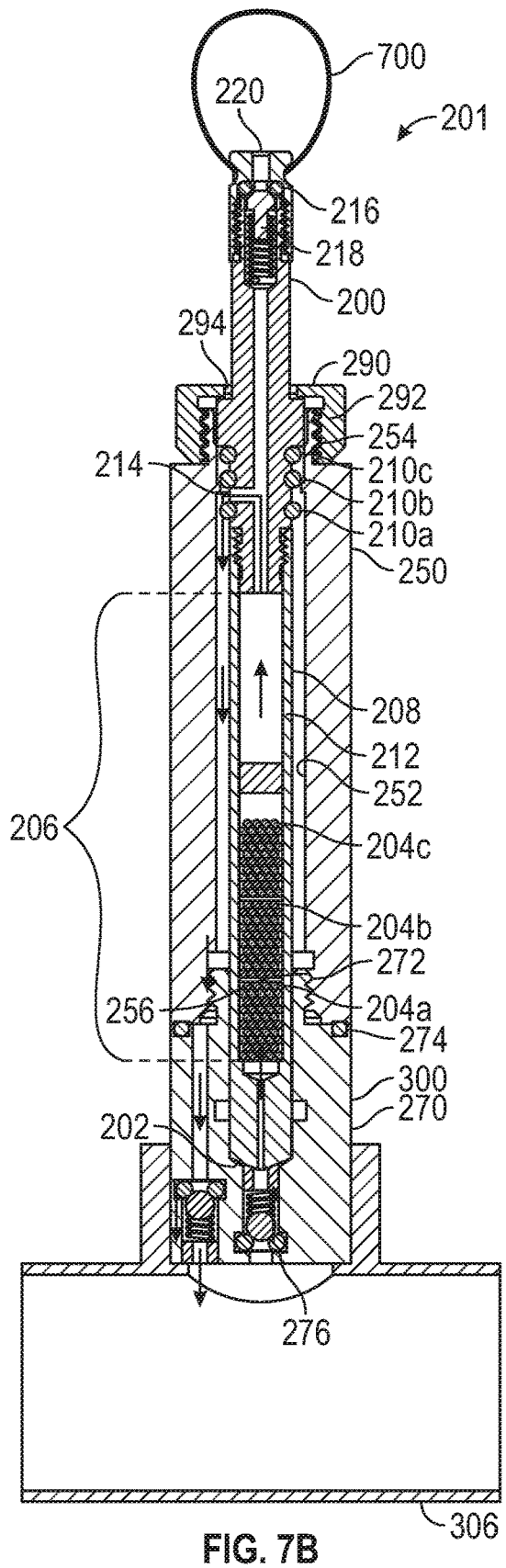

FIGS. 7A-7B illustrate another sample collection system according to some embodiments of the disclosure. The sample collection system includes the same components as the sample collection system illustrated in FIGS. 5A-5B and further includes a balloon 700 attached to the sample collection device 200. The balloon 700 is attached with a clip that opens the valve 218 of the sample collection device 200. During sampling, the balloon can be inflated and deflated to accommodate a larger volume of air inside the sample collection system than what is possible without the balloon (e.g., using the system shown in FIGS. 5A-5B). The inclusion of the balloon can also indicate that flow is occurring into and out of the sample collection device 200 as expected during sampling. As shown in FIG. 7A, during inspiration, the balloon 700 is able to inflate slightly due to the increased pressure in the sample collection system. As shown in FIG. 7B, during exhalation, the balloon 700 is able to deflate slightly due to the decreased pressure in the sample collection system. After sampling is concluded, the balloon can be discarded and a new balloon can be attached for each use of the sample collection system. When samples are not being collected, a blank sample collection device or a plug can be attached to coupling 300 to seal the ventilator outlet line.

Figure 8A:
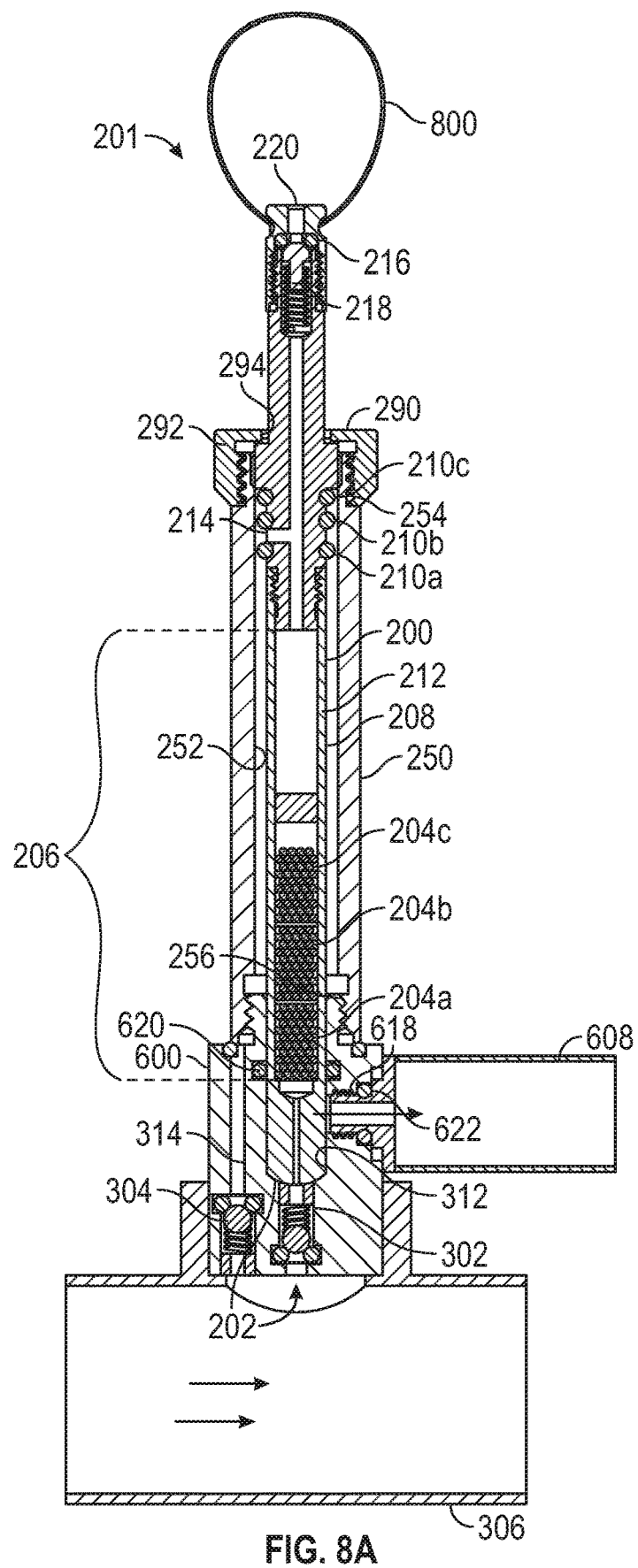
FIGS. 8A-8B illustrate another sample collection system according to some embodiments of the disclosure.
Figure 8B:
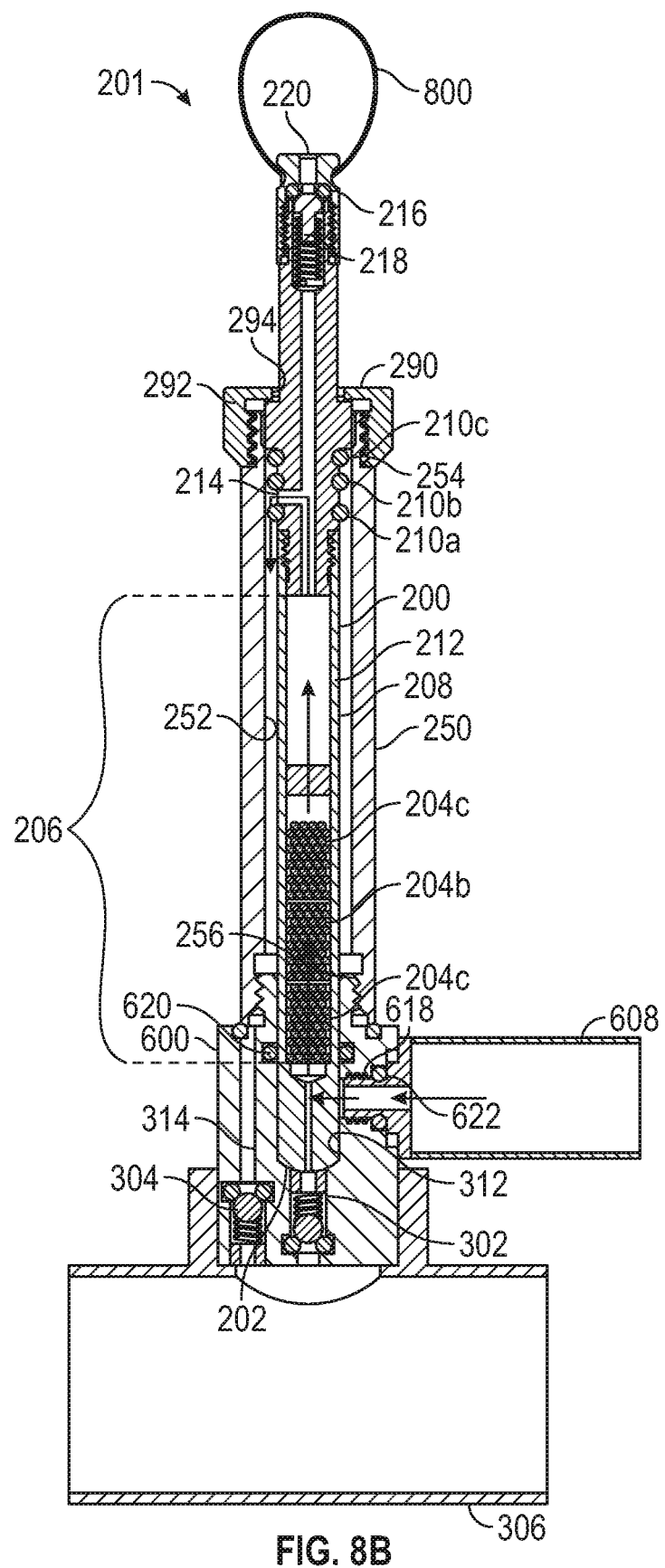

FIGS. 8A-8B illustrate another sample collection system according to some embodiments of the disclosure. The sample collection system includes the same components as the sample collection system illustrated in FIGS. 6A-6B and further includes a balloon 800 attached to the sample collection device 200. The balloon 800 is attached with a clip that opens the valve 218 of the sample collection device 200. During sampling, the balloon can be inflated and deflated to accommodate a larger volume of air inside the sample collection system than what is possible without the balloon (e.g., using the system shown in FIGS. 6A-6B). The inclusion of the balloon can also indicate that flow is occurring into and out of the sample collection device 200 as expected during sampling. As shown in FIG. 8A, during inspiration, the balloon 800 is able to inflate slightly due to the increased pressure in the sample collection system. As shown in FIG. 8B, during exhalation, the balloon 700 is able to deflate slightly due to the decreased pressure in the sample collection system. After sampling is concluded, the balloon can be discarded and a new balloon can be attached for each use of the sample collection system. When samples are not being collected, a blank sample collection device or a plug can be attached to coupling 300 to seal the ventilator outlet line.

Figure 9:
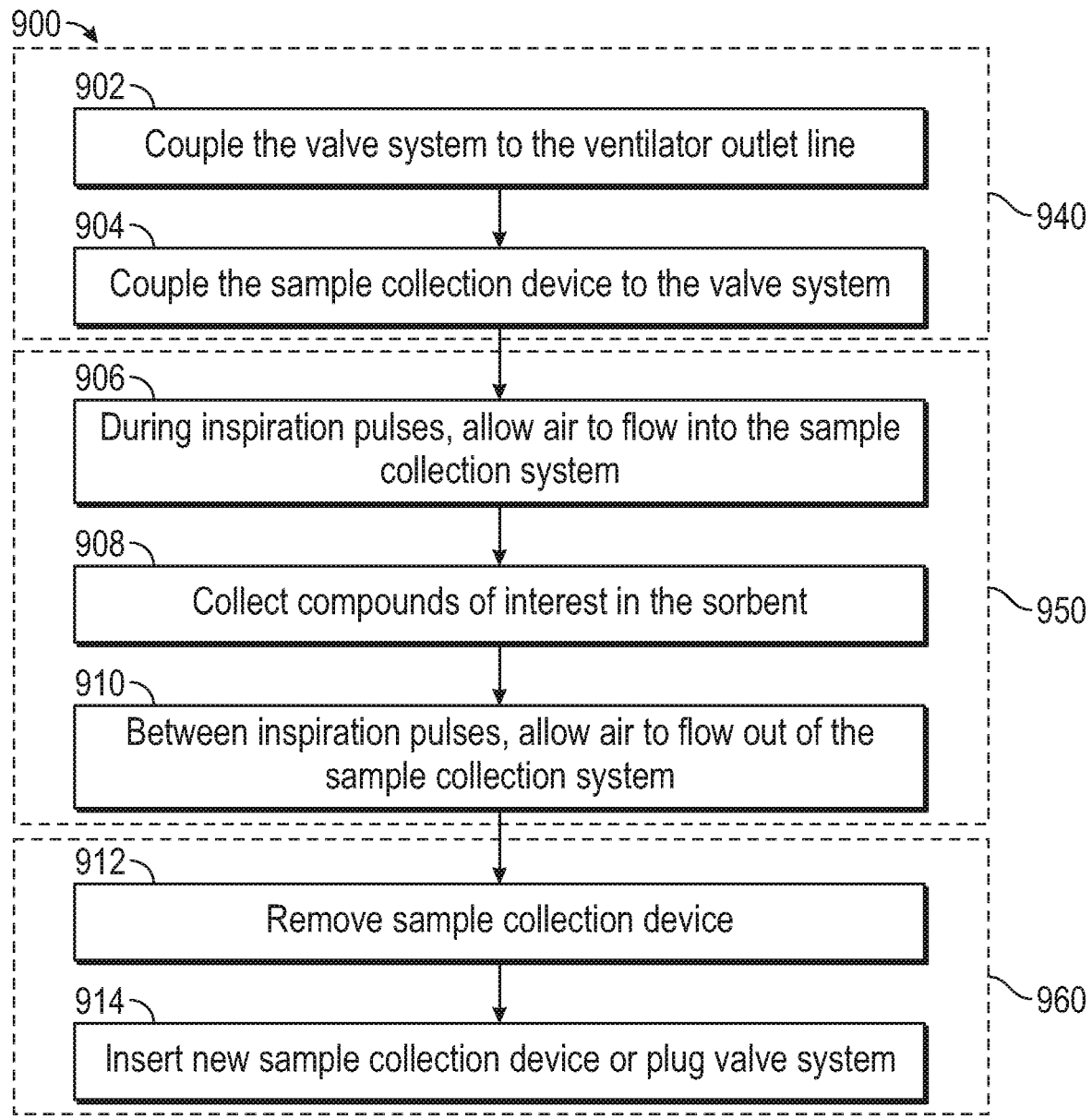
FIG. 9 illustrates a process for collecting a sample according to some embodiments of the disclosure.

FIG. 9 illustrates a process for collecting a sample according to some embodiments of the disclosure. One or more of the systems illustrated in FIGS. 2A-6B can be used to perform some or all of the steps of process 900 to collect a sample of target compounds (e.g., VOCs) from exhaled breath in a ventilator outlet line. Process 900 includes a setup process 940, a sampling process 950, and a post-sampling process 960.

Setup process 940 includes steps 902 and 904. At step 902 of process 900, the valve system (e.g., valve system of coupling 300) is coupled to the ventilator outlet line. As shown in FIG. 3A, the coupling 300 can be attached to a tee 306 that is connected to the ventilator outlet line. Coupling includes an intake one-way valve 302 and an outlet one-way valve 304, as described above.

At step 904 of process 900, the sample collection device 200 is coupled to the valve system (e.g., valve system of coupling 300). Once steps 902 and 904, which can be performed in any order, are complete, the sample collection device 200 is also coupled to the ventilator outlet line through the valve system of the coupling 300.

While the ventilator is running, a pump included in the ventilator drives the pressure in the inlet and outlet lines of the ventilator. For example, the pump can generate a pressure pattern according to FIGS. 1A, 1B, 5C, or 6C. During each inspiration pulse, pressure in the ventilator lines increases. Between inspiration pulses, pressure in the ventilator outlet lines decreases. The pressure cycle generated by the ventilator pump drives the flow of air into and out of the sample collection device 200 during steps 906 and 910, described below.

Sampling process 950 includes steps 906, 908, and 910. In step 906, an inspiration pulse occurs and air flows into the sample collection system 201 through the intake one-way valve 302 of the coupling 300. The flow into the sample collection system 201 is driven by the pressure difference between the ventilator outlet line, which can have an elevated pressure during inspiration, and the sample collection system 200. In some embodiments, such as in embodiments which include a side reservoir 608 that can hold exhaled air, flow into the sample collection system can continue after the inspiration pulse has ceased, as illustrated in FIG. 6C.

In step 908 of process 900, one or more compounds of interest (e.g., VOCs) present in the exhaled air can be collected in the sorbent 204 of the sample collection device 200. In some embodiments, such as in embodiments that do not include the optional side reservoir 608, collection occurs during the inspiration pulse. In some embodiments, such as in embodiments that include the optional side reservoir 608, collection occurs between inspiration pulses.

In step 910, which occurs between inspiration pulses of the ventilator inspiration cycle, air flows out of the sample collection device 200 and back into the ventilator outlet line. The air flows through the outlet one-way valve 304 of the coupling. The air that flows out of the sample collection system 200 has already flowed through the sorbent 204 of the sample collection system 200. Thus, air that returns to the ventilator outlet line has already been sampled.

Post-sampling process 960 includes steps 912 and 914. In step 912, the sample collection device 200 is removed from the coupling 300 or 600. The sample collection device 200 is removed from the coupling 300 or 600 after a sampling period that can last 5 to 60 minutes. After the sample collection device 200 is removed, it can be placed in the cap-and-sleeve assembly including caps 270 and 290 and sleeve 250, such as in FIG. 2B. Isolating the sample collection device 200 in this way prevents the sample from becoming contaminated by the environment external to the sorbent 204 of the sample collection device 200.

In step 914, a new sample collection device 200 is inserted into the coupling 300 or 600 or a cap or plug is applied to the coupling 300 or 600. A new sample collection device 200 can be used to collect another sample from the ventilator outlet line. A cap or plug can close the ventilator system when sample collection is not occurring.

The flow rate and flow volume through the sample collection device 200 for each breathing cycle depends on the volume between inlet one-way valve 302 and the outlet one-way valve 304. The larger that volume, the greater the volume sampled, and therefore, the greater the flow rate. The pressure change during a ventilator breath cycle is on the order of 10-15 cm H2O. As an example, suppose the pressure change during an exemplary ventilator breath cycle is 12 cm H2O, which is about 0.012 atmospheres. As an example, the sample collection device 200 is coupled to a 50 cc reservoir 608. Under these exemplary conditions, the volume of sample collected is 0.6 cc/breath. With 12 breath cycles per minute under these exemplary conditions, sampling occurs at a rate of 7.2 cc/min, resulting in 216 cc of air sampled in 30 minutes. Detecting pneumonia based on VOC levels in the lungs, for example, can be done by sampling at least 50 cc of air and analyzing the sample. Therefore, one way to use the disclosed system is to sample a volume of 10 cc -100 cc of air over the course of about 30 minutes. Without the optional reservoir 608, sampling times could be longer, but in some cases, that may be desirable. In general, the sampling flow rates can be on the order of 0.7-15 cc/min when using a reservoir 608 with a volume in the range of 5-100 cc.

Figure 10:
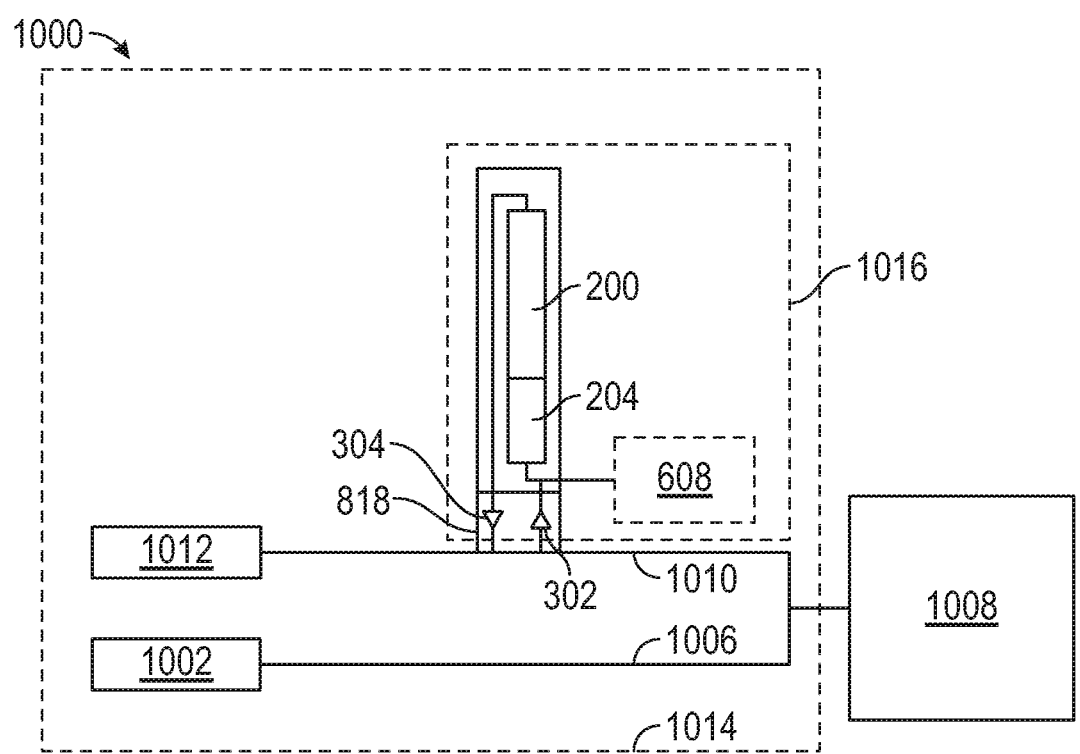
FIG. 10 illustrates a system block diagram according to some embodiments of the disclosure.

FIG. 10 illustrates a system block diagram 800 according to some embodiments of the disclosure. The block diagram 800 includes ventilator pump 1002, ventilator inlet line 1006, the patient 1008, ventilator outlet line 1010, ventilator outlet vent 1012 a valve system 818 including inlet one-way valve 302 and outlet one-way valve 304, the sample collection device 200 including a sorbent 204, and optional reservoir 608. As described above, sorbent 204 can include a plurality of sorbents (e.g., three sorbents) arranged in order of increasing strength. The valve system 818 can be included in coupling 300 or 600.

Block diagram 1000 illustrates a ventilator system 1014 that includes ventilator pump 1002, ventilator outlet vent 1012 that can open and close, ventilator inlet line 1006, ventilator outlet line 1010, a valve system 818 including inlet one-way valve 302 and outlet one-way valve 304, the sample collection device 200 including a sorbent 204, and optional reservoir 608. Additional or alternate components, such as timers, sensors, pressure regulators, and control valves, can be included in the system 1000 without departing from the scope of the disclosure. The block diagram 1000 also illustrates a sample collection system that includes a valve system 818 including inlet one-way valve 302 and outlet one-way valve 304, the sample collection device 200 including a sorbent 204, and optional reservoir 608.

Ventilator inlet line 1006 can facilitate flow of gas from the ventilator pump 1002 into the patient 1008 (e.g., and into the patient's lungs to support the patient's breathing). The patient 1008 is also fluidly coupled to the ventilator outlet line 1010. The ventilator outlet line 1010 can facilitate flow of gas from the patient 1008 to the ventilator outlet vent 1012. Because the ventilator inlet line 1006, ventilator outlet line 1010, and the patient 1008 are in fluid communication with one another, when the pressure of the ventilator inlet line 1006 is increased by the ventilator pump 1002, the pressure in the ventilator outlet line 1010 also increases. The periodic increase of pressure in the ventilator outlet line 1010, which is driven by the ventilator pump 1002, drives the flow of gas into the sample collection system 1016, while the reduction in pressure in between inspiration pulses allows the return of the extracted breath sample into the exhaust line for ultimate delivery to the ventilator vent 1012, leaving the VOCs trapped on the sampler adsorbent. Ventilator outlet vent 1012 can be a valve or a similar mechanism that opens between inspiration pulses driven by the ventilator pump 1002 and closes during the inspiration pulses. In this way, pressure is allowed to decrease in the ventilator inlet line 1006, the ventilator outlet line 1010, and the patient 1008 between inspiration pulses, during exhalation. In some embodiments, alternative means of decreasing the pressure in the ventilator system between inspiration pulses are possible without departing from the scope of the disclosure.

Therefore, according to the above, some embodiments of the disclosure are directed to a ventilator diagnostic VOC sample collection system comprising: a sample collection device, the sample collection device including a cavity containing one or more sorbents; and a valve system coupled to an opening of the cavity of the sample collection system, the valve system comprising a first one-way valve that allows flow of gas into the sample collection system and a second one-way valve that allows flow of gas out of the sample collection system, wherein: the valve system is configured to be coupled to a ventilator outlet line, the sample collection system is configured to allow the flow of gas into the sample collection system to occur during periodic inspiration pulses of an inspiration cycle of the ventilator, the sample collection system is configured to allow the flow of gas out of the sample collection system to occur between the inspiration pulses of the inspiration cycle of the ventilator, a pump of the ventilator increases pressure in the ventilator outlet line during the inspiration pulses of the ventilator, the flow of gas into the sample collection system is actuated by the pump of the ventilator that is coupled to the sample collection system by way of the ventilator outlet line, and the flow of gas out of the sample collection system is facilitated by an outlet valve of the ventilator. Additionally or alternatively, in some embodiments, the ventilator diagnostic VOC sample collection system further includes: a sleeve having a volume, wherein the sleeve is configured to accommodate the sample collection device and configured to be coupled to the valve system. Additionally or alternatively, in some embodiments, the volume of the sleeve includes a fluid conveyance from a port of the sample collection device to the second one-way valve of the valve system, wherein: a distance between the one or more sorbents and the opening of the cavity of the sample collection system is less than a distance between the port and the opening of the cavity of the sample collection system. Additionally or alternatively, in some embodiments, the ventilator diagnostic VOC sample collection system further includes: a reservoir fluidly coupled to the first one-way valve of the valve system and the opening of the cavity of the sample collection device. Additionally or alternatively, in some embodiments, the sample collection system is further configured to: allow the flow of gas into the reservoir during the inspiration pulses; and allow the flow of gas out of the reservoir and into the sample collection device between the inspiration pulses. Additionally or alternatively, in some embodiments, the sample extraction system does not include a pump other than the pump of the ventilator. Additionally or alternatively, in some embodiments, the gas is exhaled air. Additionally or alternatively, in some embodiments, the ventilator diagnostic VOC sample collection system further includes a sampling indicator, wherein the sampling indicator is one of a balloon, a diaphragm, a switch, a pressure gauge, or a pressure sensor.

Some embodiments of the disclosure are directed to a ventilator system comprising: an outlet line; and a pump configured to increase pressure in the outlet line of the ventilator during periodic inspiration pulses of an inspiration cycle of the ventilator; and a sample collection system comprising: a sample collection device, the sample collection device including a cavity containing one or more sorbents; and a valve system coupled to an opening of the cavity of the sample collection system, the valve system comprising a first one-way valve that allows flow of gas into the sample collection system and a second one-way valve that allows flow of gas out of the sample collection system, wherein: the valve system is configured to be coupled to the ventilator outlet line, the sample collection system is configured to allow the flow of gas into the sample collection system to occur during the periodic inspiration pulses of the inspiration cycle of the ventilator, the sample collection system is configured to allow the flow of gas out of the sample collection system to occur between the inspiration pulses of the inspiration cycle of the ventilator, the flow of gas into the sample collection system is actuated by the pump of the ventilator that is coupled to the sample collection system by way of the ventilator outlet line, and the flow of gas out of the sample collection system is facilitated by an outlet valve of the ventilator. Additionally or alternatively, in some embodiments, the ventilator system of claim further comprises: a sleeve having a volume, wherein the sleeve is configured to accommodate the sample collection device and configured to be coupled to the valve system. Additionally or alternatively, in some embodiments, the volume of the sleeve includes a fluid conveyance from a port of the sample collection device to the second one-way valve of the valve system, wherein: a distance between the one or more sorbents and the opening of the cavity of the sample collection system is less than a distance between the port and the opening of the cavity of the sample collection system. Additionally or alternatively, in some embodiments, the ventilator system of claim 9, further comprising: a reservoir fluidly coupled to the first one-way valve of the valve system and the opening of the cavity of the sample collection device. Additionally or alternatively, in some embodiments, the sample collection system is further configured to: allow the flow of gas into the reservoir during the inspiration pulses; and allow the flow of gas out of the reservoir and into the sample collection device between the inspiration pulses. Additionally or alternatively, in some embodiments, the sample extraction system does not include a pump other than the pump of the ventilator. Additionally or alternatively, in some embodiments, the gas is exhaled air. Additionally or alternatively, in some embodiments, the ventilator system further includes a sampling indicator, wherein the sampling indicator is one of a balloon, a diaphragm, a switch, a pressure gauge, or a pressure sensor.

In some embodiments, a method comprises: increasing, with a pump of a ventilator that is fluidly coupled to an outlet line of the ventilator, pressure in the outlet line of the ventilator during periodic inspiration pulses of an inspiration cycle of the ventilator; during the periodic inspiration pulses of the inspiration cycle of the ventilator, actuating, with the pump of the ventilator, the flow of gas into a sample collection system; and between the periodic inspiration pulses of the inspiration cycle of the ventilator, facilitating, with an outlet valve of the ventilator, the flow of gas out of the sample collection system, wherein: the sample collection system is fluidly coupled to a valve system, the valve system is fluidly coupled to the outlet line of the ventilator, the sample collection device comprises a cavity containing one or more sorbents, and the valve system comprises a first one-way valve that allows flow of gas into the sample collection system and a second one-way valve that allows flow of gas out of the sample collection system. Additionally or alternatively, in some embodiments, the sample collection system further comprises a sleeve having a volume, wherein the sleeve is configured to accommodate the sample collection device and configured to be coupled to the valve system. Additionally or alternatively, in some embodiments, the volume of the sleeve includes a fluid conveyance from a port of the sample collection device to the second one-way valve of the valve system, wherein: a distance between the one or more sorbents and the opening of the cavity of the sample collection system is less than a distance between the port and the opening of the cavity of the sample collection system. Additionally or alternatively, in some embodiments, the sample collection system further comprises a reservoir fluidly coupled to the first one-way valve of the valve system and the opening of the cavity of the sample collection device. Additionally or alternatively, in some embodiments, the sample collection system configured to: allow the flow of gas into the reservoir during the inspiration pulses; and allow the flow of gas out of the reservoir and into the sample collection device between the inspiration pulses. Additionally or alternatively, in some embodiments, the sample extraction system does not include a pump other than the pump of the ventilator. Additionally or alternatively, in some embodiments, the gas is exhaled air. Additionally or alternatively, in some embodiments, the method further includes indicating, with a sampling indicator, a change in pressure in the sample collection system, wherein the sampling indicator is one of a balloon, a diaphragm, a switch, a pressure gauge, or a pressure sensor.

Although examples have been fully described with reference to the accompanying drawings, it is to be noted that various changes and modifications will become apparent to those skilled in the art. Such changes and modifications are to be understood as being included within the scope of examples of this disclosure as defined by the appended claims.

What is claimed as new and desired to be protected by Letters Patent of the United States is:

1. A ventilator diagnostic VOC sample collection system comprising:
   a sample collection device, the sample collection device including a cavity containing one or more sorbents;
   a valve system coupled to an opening of the cavity of the sample collection system, the valve system comprising a first one-way valve that allows flow of gas into the sample collection system and a second one-way valve that allows flow of gas out of the sample collection system; and
   a sleeve having a volume including a fluid conveyance from a port of the sample collection device to the second one-way valve of the valve system, the sleeve being configured to accommodate the sample collection device and configured to be coupled to the valve system, wherein:
the valve system is configured to be coupled to a ventilator outlet line,
the sample collection system is configured to allow the flow of gas into the sample collection system to occur during periodic inspiration pulses of an inspiration cycle of the ventilator,
the sample collection system is configured to allow the flow of gas out of the sample collection system to occur between the inspiration pulses of the inspiration cycle of the ventilator,
a pump of the ventilator increases pressure in the ventilator outlet line during the inspiration pulses of the ventilator,
the flow of gas into the sample collection system is actuated by the pump of the ventilator that is coupled to the sample collection system by way of the ventilator outlet line,
the flow of gas out of the sample collection system is facilitated by an outlet valve of the ventilator, and
a distance between the one or more sorbents and the opening of the cavity of the sample collection system is less than a distance between the port and the opening of the cavity of the sample collection system.

2. The ventilator diagnostic VOC sample collection system of claim 1, further comprising:
a reservoir fluidly coupled to the first one-way valve of the valve system and the opening of the cavity of the sample collection device.

3. The ventilator diagnostic VOC sample collection system of claim 2, wherein the sample collection system is further configured to:
allow the flow of gas into the reservoir during the inspiration pulses; and
allow the flow of gas out of the reservoir and into the sample collection device between the inspiration pulses.

4. The ventilator diagnostic VOC sample collection system of claim 1, wherein the sample collection system does not include a pump other than the pump of the ventilator.

5. The ventilator diagnostic VOC sample collection system of claim 1, wherein the gas is exhaled air.

6. The ventilator diagnostic VOC sample collection system of claim 1, further comprising a sampling indicator, wherein the sampling indicator is one of a balloon, a diaphragm, a switch, a pressure gauge, or a pressure sensor.

7. A ventilator system comprising:
an outlet line; and
a pump configured to increase pressure in the outlet line of the ventilator during periodic inspiration pulses of an inspiration cycle of the ventilator; and
a sample collection system comprising:
a sample collection device, the sample collection device including a cavity containing one or more sorbents;
a valve system coupled to an opening of the cavity of the sample collection system, the valve system comprising a first one-way valve that allows flow of gas into the sample collection system and a second one-way valve that allows flow of gas out of the sample collection system; and
a sleeve having a volume including a fluid conveyance from a port of the sample collection device to the second one-way valve of the valve system, the sleeve being configured to accommodate the sample collection device and configured to be coupled to the valve system, wherein:
the valve system is configured to be coupled to the ventilator outlet line,
the sample collection system is configured to allow the flow of gas into the sample collection system to occur during the periodic inspiration pulses of the inspiration cycle of the ventilator,
the sample collection system is configured to allow the flow of gas out of the sample collection system to occur between the inspiration pulses of the inspiration cycle of the ventilator,
the flow of gas into the sample collection system is actuated by the pump of the ventilator that is coupled to the sample collection system by way of the ventilator outlet line,
the flow of gas out of the sample collection system is facilitated by an outlet valve of the ventilator, and
a distance between the one or more sorbents and the opening of the cavity of the sample collection system is less than a distance between the port and the opening of the cavity of the sample collection system.

8. The ventilator system of claim 7, further comprising:
a reservoir fluidly coupled to the first one-way valve of the valve system and the opening of the cavity of the sample collection device.

9. The ventilator system of claim 8, wherein the sample collection system is further configured to:
allow the flow of gas into the reservoir during the inspiration pulses; and
allow the flow of gas out of the reservoir and into the sample collection device between the inspiration pulses.

10. The ventilator system of claim 7, wherein the sample collection system does not include a pump other than the pump of the ventilator.

11. The ventilator system of claim 7, wherein the gas is exhaled air.

12. The ventilator system of claim 7, further comprising a sampling indicator, wherein the sampling indicator is one of a balloon, a diaphragm, a switch, a pressure gauge, or a pressure sensor.

13. A method comprising:
increasing, with a pump of a ventilator that is fluidly coupled to an outlet line of the ventilator, pressure in the outlet line of the ventilator during periodic inspiration pulses of an inspiration cycle of the ventilator;
during the periodic inspiration pulses of the inspiration cycle of the ventilator, actuating, with the pump of the ventilator, [[the]] flow of gas into a sample collection system; and
between the periodic inspiration pulses of the inspiration cycle of the ventilator, facilitating, with an outlet valve of the ventilator, the flow of gas out of the sample collection system, wherein:
the sample collection system is fluidly coupled to a valve system,
the valve system is fluidly coupled to the outlet line of the ventilator,
the sample collection system comprises a sample extraction device having a cavity containing one or more sorbents, and
the valve system comprises a first one-way valve that allows flow of gas into the sample collection system and a second one-way valve that allows flow of gas out of the sample collection system.

14. The method of claim 13, wherein:
the sample collection system further comprises a sleeve having a volume, wherein the sleeve is configured to accommodate the sample collection device and configured to be coupled to the valve system.

15. The method of claim 14, wherein:
the volume of the sleeve includes a fluid conveyance from a port of the sample collection device to the second one-way valve of the valve system, wherein:
a distance between the one or more sorbents and an opening of the cavity of the sample collection system is less than a distance between the port and the opening of the cavity of the sample collection system.

16. The method of claim 13, wherein:
the sample collection system further comprises a reservoir fluidly coupled to the first one-way valve of the valve system and an opening of the cavity of the sample collection device.

17. The method of claim 13, wherein the sample collection system configured to:
allow the flow of gas into a reservoir of the sample collection system during the inspiration pulses; and
allow the flow of gas out of the reservoir and into the sample collection device between the inspiration pulses.

18. The method of claim 13, wherein the sample collection system does not include a pump other than the pump of the ventilator.

19. The method of claim 13, wherein the gas is exhaled air.

20. The method of claim 13, further comprising:
indicating, with a sampling indicator, a change in pressure in the sample collection system, wherein the sampling indicator is one of a balloon, a diaphragm, a switch, a pressure gauge, or a pressure sensor.

* * * * *